US010334930B2

(12) United States Patent
Toeg et al.

(10) Patent No.: US 10,334,930 B2
(45) Date of Patent: Jul. 2, 2019

(54) NAIL SANITIZER TOOL

(71) Applicant: Freshnails Sanitizer Inc., Ottawa (CA)

(72) Inventors: Bayan (Ben) Toeg, Ottawa (CA); Sayed Dadshani, Ottawa (CA); Gilad Shoham, Toronto (CA)

(73) Assignee: Freshnails Sanitizer, Inc., Ottawa (CA)

( * ) Notice: Subject to any disclaimer, the term of this patent is extended or adjusted under 35 U.S.C. 154(b) by 169 days.

(21) Appl. No.: 14/555,009

(22) Filed: Nov. 26, 2014

(65) Prior Publication Data

US 2015/0144150 A1    May 28, 2015

Related U.S. Application Data

(60) Provisional application No. 61/909,120, filed on Nov. 26, 2013.

(51) Int. Cl.
*A45D 29/17*    (2006.01)
*A61L 2/18*    (2006.01)

(52) U.S. Cl.
CPC ........... *A45D 29/17* (2013.01); *A61L 2/18* (2013.01); *A61L 2202/15* (2013.01); *A61L 2202/16* (2013.01)

(58) Field of Classification Search
CPC ........ A45D 29/00; A45D 29/16; A45D 29/17; A45D 29/06; A45D 2200/1009; A45D 2200/1018; A61L 2/18; A61L 2/26
USPC ... 15/104.93, 104.92, 167.3, 236.01, 236.07; 401/198, 199, 196, 202, 207
See application file for complete search history.

(56) References Cited

U.S. PATENT DOCUMENTS

| | | | | |
|---|---|---|---|---|
| 4,886,078 A * | 12/1989 | Shiffman | ............... | A45D 29/17 132/73 |
| 4,944,318 A * | 7/1990 | Gaylord, Jr. | ......... | A45D 34/045 132/320 |
| 7,011,466 B2 * | 3/2006 | Iida | .......................... | B43K 5/03 401/198 |
| 8,337,913 B1 * | 12/2012 | Picazo | ..................... | A61K 8/44 424/411 |
| 2006/0196519 A1 * | 9/2006 | Strickland | .............. | A45D 29/17 132/73.5 |
| 2013/0133677 A1 * | 5/2013 | Hwang | .................. | A45D 29/11 132/75.6 |
| 2015/0272295 A1 * | 10/2015 | Stine | ...................... | A45D 29/16 132/73 |

(Continued)

OTHER PUBLICATIONS

Neither the Applicant nor the undersigned is aware of any prior art devices or documents which are believed to be material to the invention as claimed. This document is being supplied for informational purposes to the Examiner and is evidence of our desire to comply with the duty of disclosure.

*Primary Examiner* — Tatiana L Nobrega
(74) *Attorney, Agent, or Firm* — Timothy D. Bennett; Emerson Thomson Bennett

(57) ABSTRACT

This invention is a product used in the delivery of a sanitization agent for sanitizing the under-the-fingernail (UTF) region. This product allows for: the keeping of a sanitization agent to be applied through the use of a nib; access to disposable nibs and a digger to remove objects in the UTF region. The sanitizing agent is applied through the nib for sanitization and disinfection of bacteria, viruses, common germs and other bodily-infecting agents.

6 Claims, 25 Drawing Sheets

(56) References Cited

U.S. PATENT DOCUMENTS

2016/0135657 A1\* 5/2016 Mao ..................... A45D 29/11
433/89

\* cited by examiner

NAIL SANITIZER TOOL

This application claims priority to U.S. Ser. No. 61/909,120, entitled NAIL SANITIZER TOOL filed Nov. 26, 2013, which is incorporated herein by reference.

FIELD OF THE INVENTION

The present invention relates to the field of sanitizers, and more specifically sanitizers for the underside of finger and toe nails.

BACKGROUND

The most common method used to eradicate potential germs, bacteria, viruses and other biological agents, so far, is hand washing. However it has been shown in Center for Disease Control (CDC) studies that this does little to make contact and to kill bacteria lodged in the under the fingernail (UTF) region. Another popular method is that of rubber latex gloves; however gloves are tedious to use and from preliminary research, are not used at all times and instances where bacteria may come in contact with the UTF region. They are also extremely expensive and not practical to be worn by everyone at all times.

Sanitizers, and hand sanitizing in particular, have become increasingly popular in the last decade. Hand sanitizers are present in hospitals around the world, carried in people's bags, used before meals, etc. The increased focus on sanitation and keeping hands clean has led to a boom in the market and the release of a plethora of products that deal with said type of sanitation.

Most products in the market today involve an alcoholic liquid or foam that is extracted from a container and applied to one's hands. Application consists of lathering the alcoholic liquid on the external surface of the hand. Indeed, products such as these eliminate potential germs, bacteria, viruses and other biological agents from the surface of the hands. They have little impact on germs, bacteria, viruses and other biological agents in regions of the hand that are not readily accessible by surface cleaning, like the UTF. Such areas will maintain high germ, bacteria, virus, and biological agent cultures after application of today's products.

As such, there is a need for a device that can overcome the problems as enumerated above, while providing a quick, easy mechanism to sanitize the hands.

This product contains a quick and efficient method for delivering a sanitizing agent to the UTF; a product related to effective bacteria termination and UTF infections; decreases the number and power of bacteria in the UTF region that can infect and create health issues. One of the "value propositions" of this product is that water, an intermediary agent that dissolves soap or cleaning agents, must not be used. The germs and bacteria will be killed by sanitizing agents and dissipated from the UTF region by process of evaporation upon the application of this product's sanitizing agent (held for release) and the method of swabbing with its applicator.

This new product also comes at an excellent juncture in time, for a health and clinical standpoint, as hospitals around the world and particularly in North America are demanding stringent sanitization methods because of bacterial disease spreading. The lack of hand-sanitization, as corroborated by CDC document research, can lead to minor issues such as absenteeism, and possible major issues, such as severe respiratory illness and severe sickness.

Based on hand-sanitation industry analysis, the need for an "under-the-fingernail sanitization applicator and method" is an excellent step to achieving and meeting world-wide health agency's goals of hand-sanitation levels.

This product addresses a healthcare issue. There can be an accumulation of foreign particles and bacteria under the fingernail that when transmitted, can result in illness and disease. This residue actively enters the body by way of using the under-the-fingernail (UTF) cavity as a holding reservoir. These infective agents then penetrate into the body through orifices such as the eye, mouth, ear, nasal cavities and open wounds. These infective agents must be eliminated through an applicator and method that can reach the under-the-fingernail region and sanitize this region. This is a problem especially for those who work in, but not limited to, the healthcare, childcare, and food services industries.

There is currently no product or method in use that targets the specific sanitization and disinfection of the under-the-fingernail area.

SUMMARY

The following invention is for a nail sanitizing tool comprising a main body housing a wadding section, a nib, and a digger directly opposed to the nib wherein the nib and digger are able to penetrate a region under a fingernail.

BRIEF DESCRIPTION OF THE DRAWINGS

It will now be convenient to describe the invention with particular reference to one embodiment of the present invention. It will be appreciated that the drawings relate to one embodiment of the present invention only and are not to be taken as limiting the invention.

FIG. 4a is a profile view of the digger protrusion, according to one embodiment of the present invention;

FIG. 5a is an enlarged frontal view of a triangular zone on the pointed top of the digger, according to one embodiment of the present invention;

DETAILED DESCRIPTION

The present invention will now be described more fully hereinafter with reference to the accompanying drawings, in which preferred and other embodiments of the invention are shown. No embodiment described below limits any claimed invention and any claimed invention may cover processes or apparatuses that are not described below. The claimed inventions are not limited to apparatuses or processes having all the features of any one apparatus or process described below or to features common to multiple or all of the apparatuses described below. It is possible that an apparatus or process described below is not an embodiment of any claimed invention. The applicants, inventors or owners reserve all rights that they may have in any invention claimed in this document, for example the right to claim such an invention in a continuing application and do not intend to abandon, disclaim or dedicate to the public any such invention by its disclosure in this document.

Figure 1:
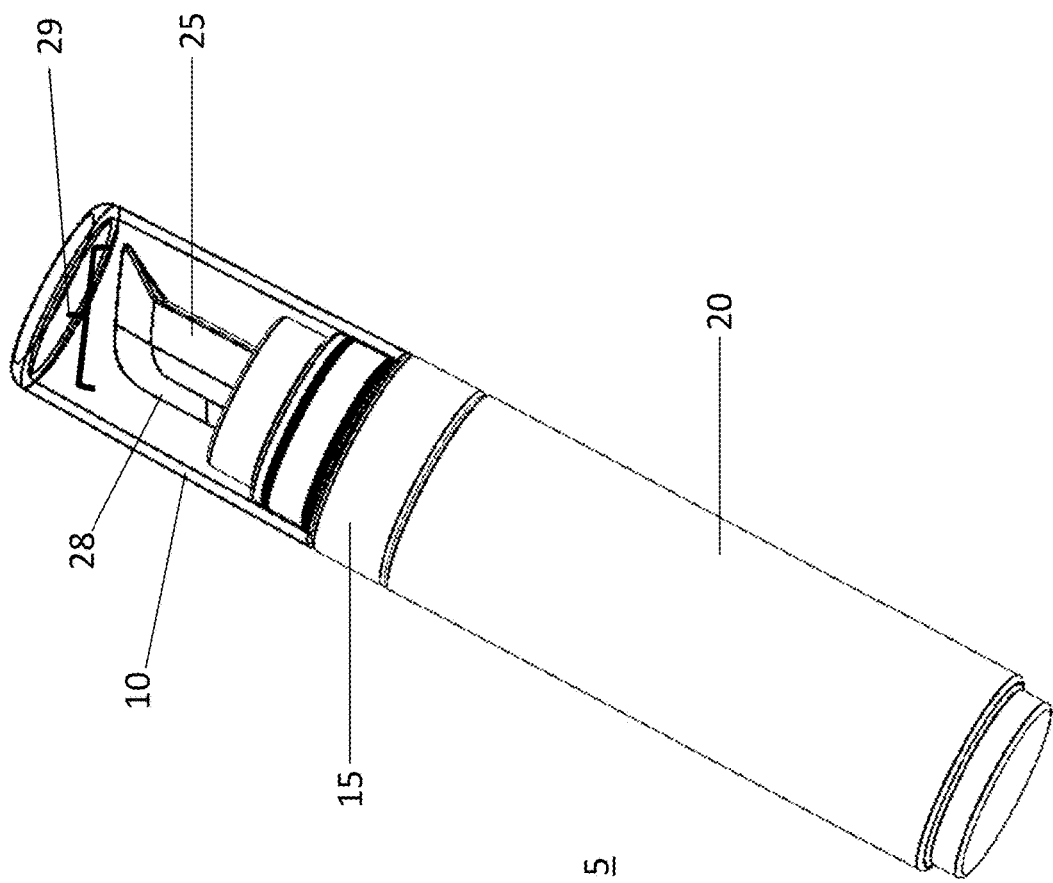
FIG. 1 is a perspective view of a nail sanitizer tool, according to one embodiment of the present invention.

With reference to FIG. 1 and according to one embodiment of the present invention, the nail sanitizer tool 5 is shown in greater detail. The nail sanitizer tool 5 is primarily comprised of a main body 20 housing a wadding section (not shown) to store alcohol, a cap 10, a nib holder 15, a digger 25 and a nib 28 interconnected to the main body 20. The digger 25 and the nib 28 are operatively coupled to one another and are collectively called the nail penetrating device 29. The digger 25 and nib 28 are directly opposed to one another. The purpose of the nail sanitizer tool 5 is to clean and sanitize the UTF region in a two-step process. Firstly, the nail sanitizer tool 5 removes debris from the UTF with the digger 25. Secondly, nail sanitizer tool 5 sanitizes the UTF with sanitization saturated nib 28. In a continuous motion the digger 25 is passed through the UTF. The digger 25 penetrates the UTF at one corner of the nail and is run along the opening to the other corner of the nail. Upon reaching the opposite corner, the nail penetrating device 29 is rotated while maintaining contact with the UTF. As a result of the rotation, the nib 28 is now in the region defined as UTF. The nail sanitizer tool 5 is run along the finger nail once more, passing the nib 28 through the UTF, and returning the nail sanitizer tool 5 to the initial point of contact on the nail and UTF. The nib 28 is specifically contoured to fit the under the fingernail region. It has been designed, developed, tried and tested to be angled, contoured and chiseled perfectly to fit and penetrate this region.

Figure 2:
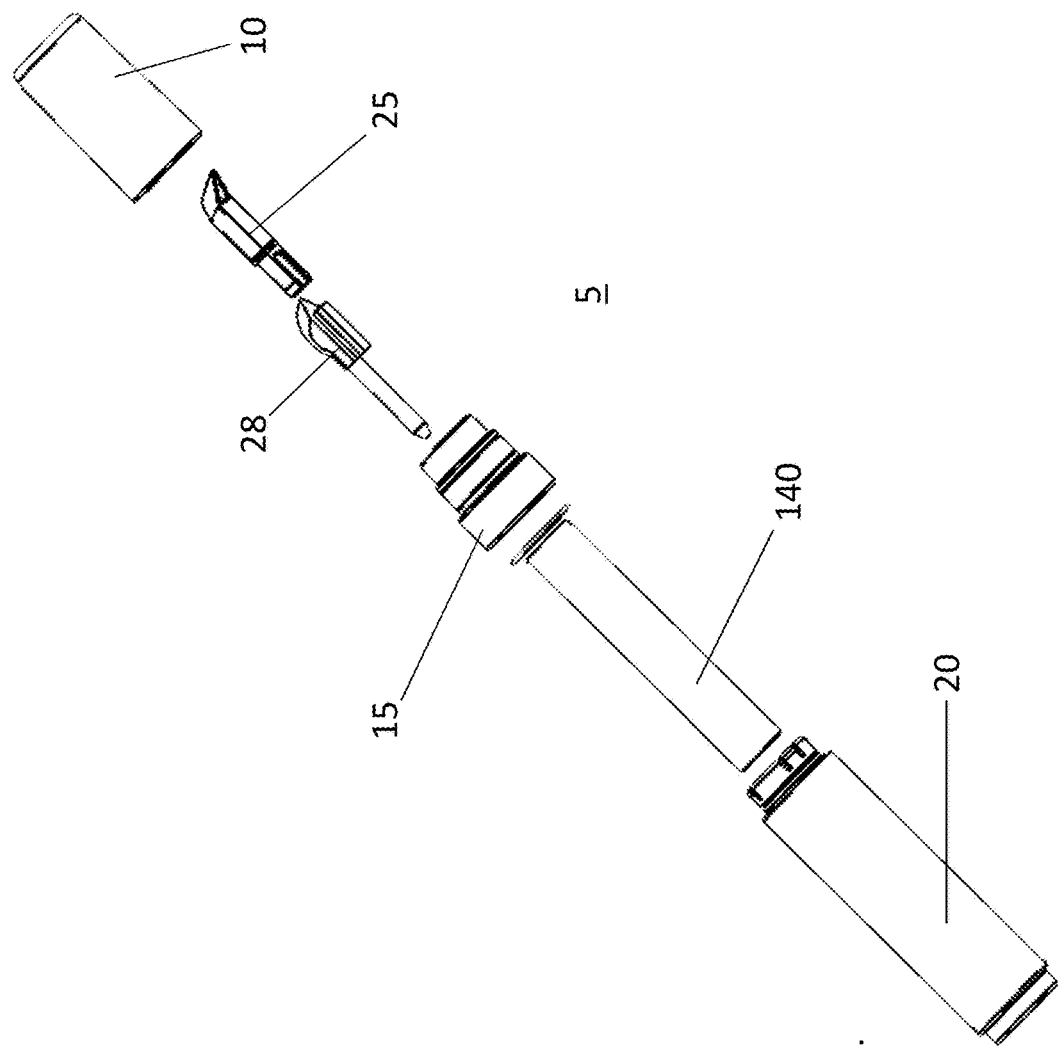
FIG. 2 is an exploded view of a nail sanitizer tool, according to one embodiment of the present invention.

With reference to FIG. 2, and according to one embodiment of the present invention the components of the nail sanitizer tool 5 are described in greater detail. Nail sanitizer tool 5 is shown in an exploded view. The nail sanitizer tool 5 consists of, the main body 20, cap 10, nib holder 15, digger 25 and nib 28, and wadding section 140. The wadding section 140 is housed within the main body 20. The digger 25 is coupled onto the nib 28 and together attach to the nib holder 15. The nib holder 15 is securely fastened onto the main body 20. The cap 10 is secured onto the nib holder 15.

Figure 3:
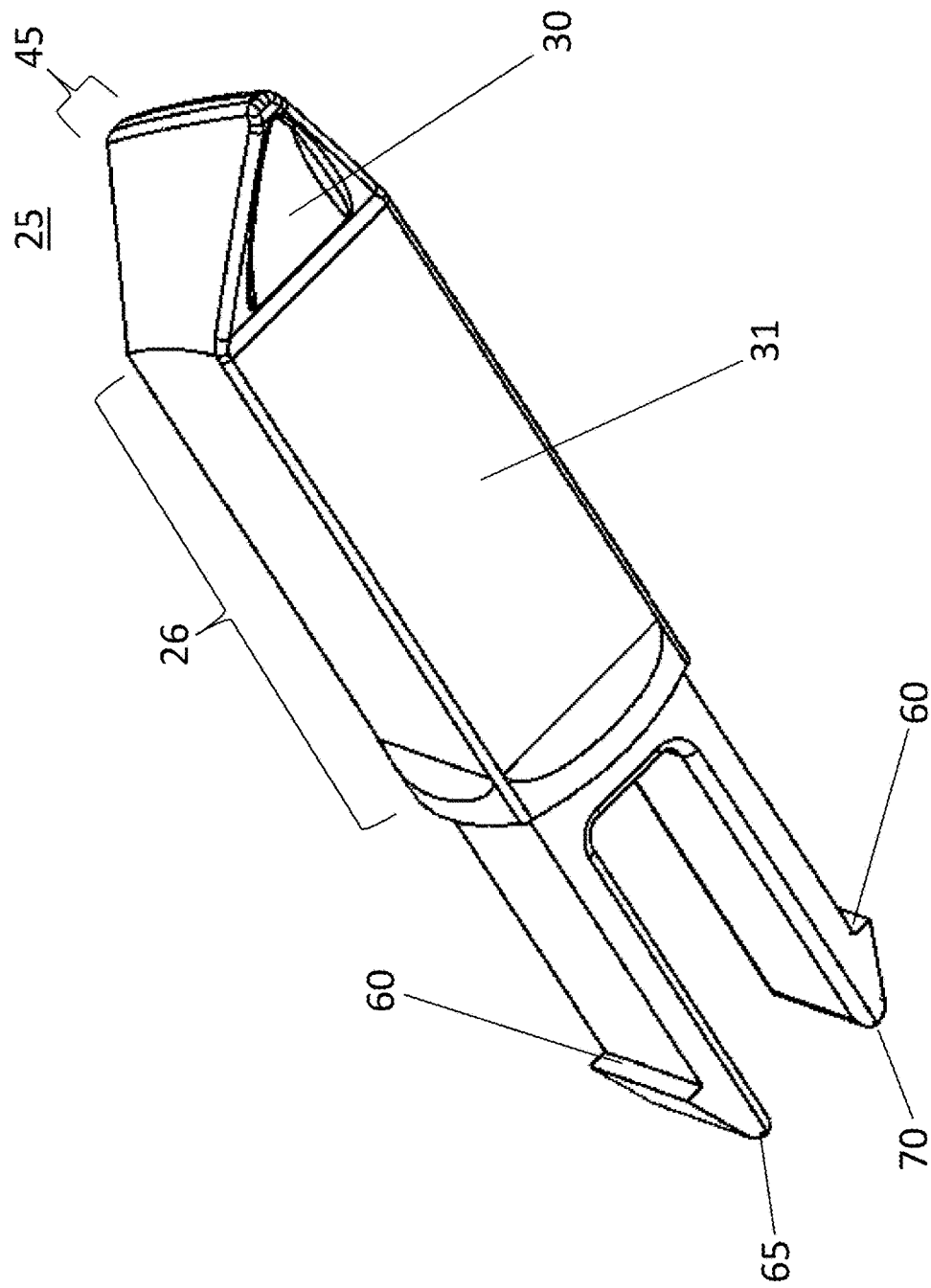
FIG. 3 is a perspective view of a digger as used in nail sanitizer tool, according to one embodiment of the present invention.

With reference to FIG. 3 and according to one embodiment of the present invention the digger 25 is shown in greater detail. The digger 25 is comprised of a body 26 and first and second arms, 65 and 70. Said body 26 of the digger 25 attenuates to a rounded edge 45. The triangular zone 55 contains a concave cavity 30 on the face of the body 31. The first and second arm, 65 and 70, contain extruding latch 60. In one embodiment, the digger is composed of plastic. In another embodiment the digger is composed of plastic and sponge. In a further embodiment, the digger is composed of sponge materials only.

Figure 4:
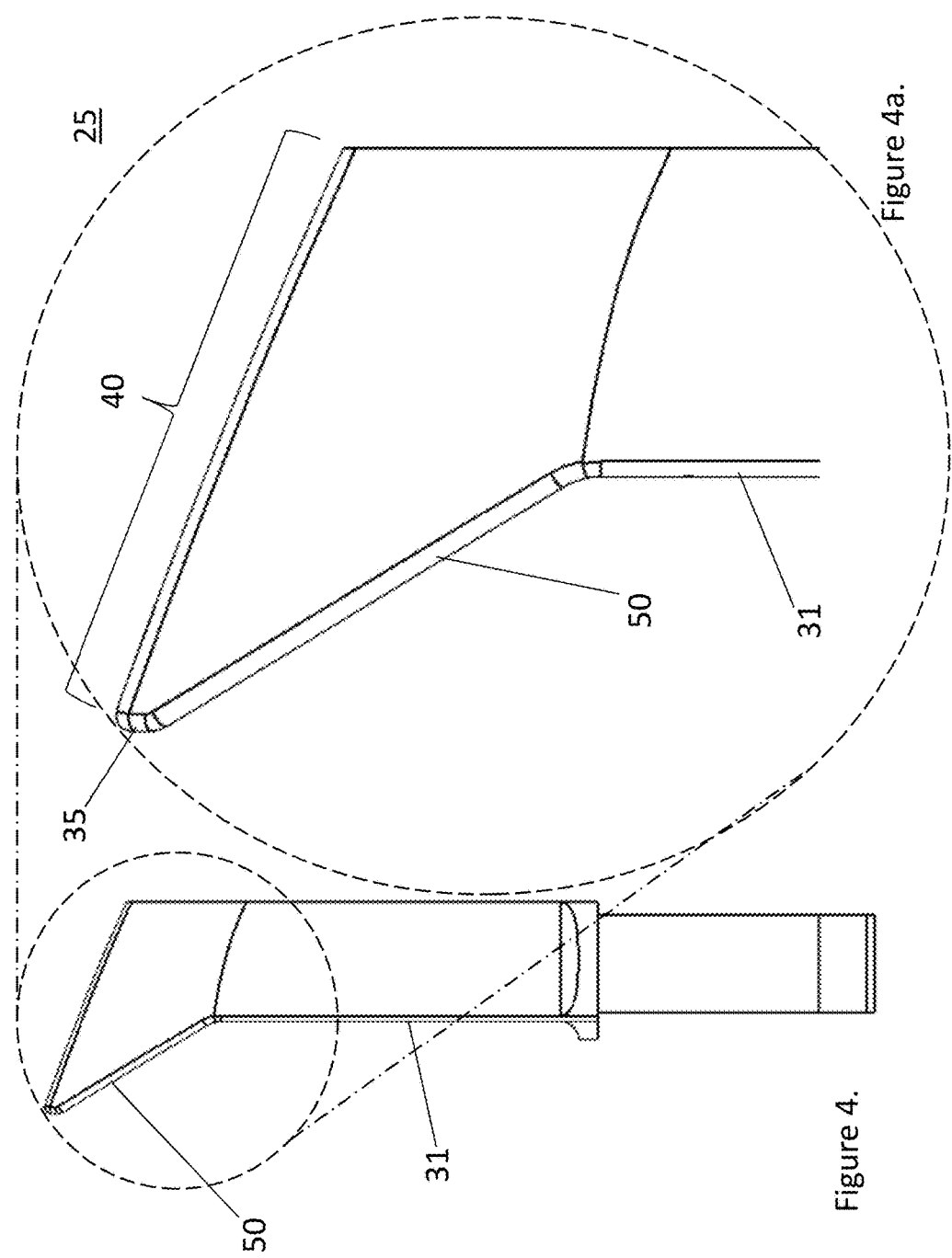
FIG. 4 is a profile view of a digger, according to one embodiment of the present invention.
Figure 5:
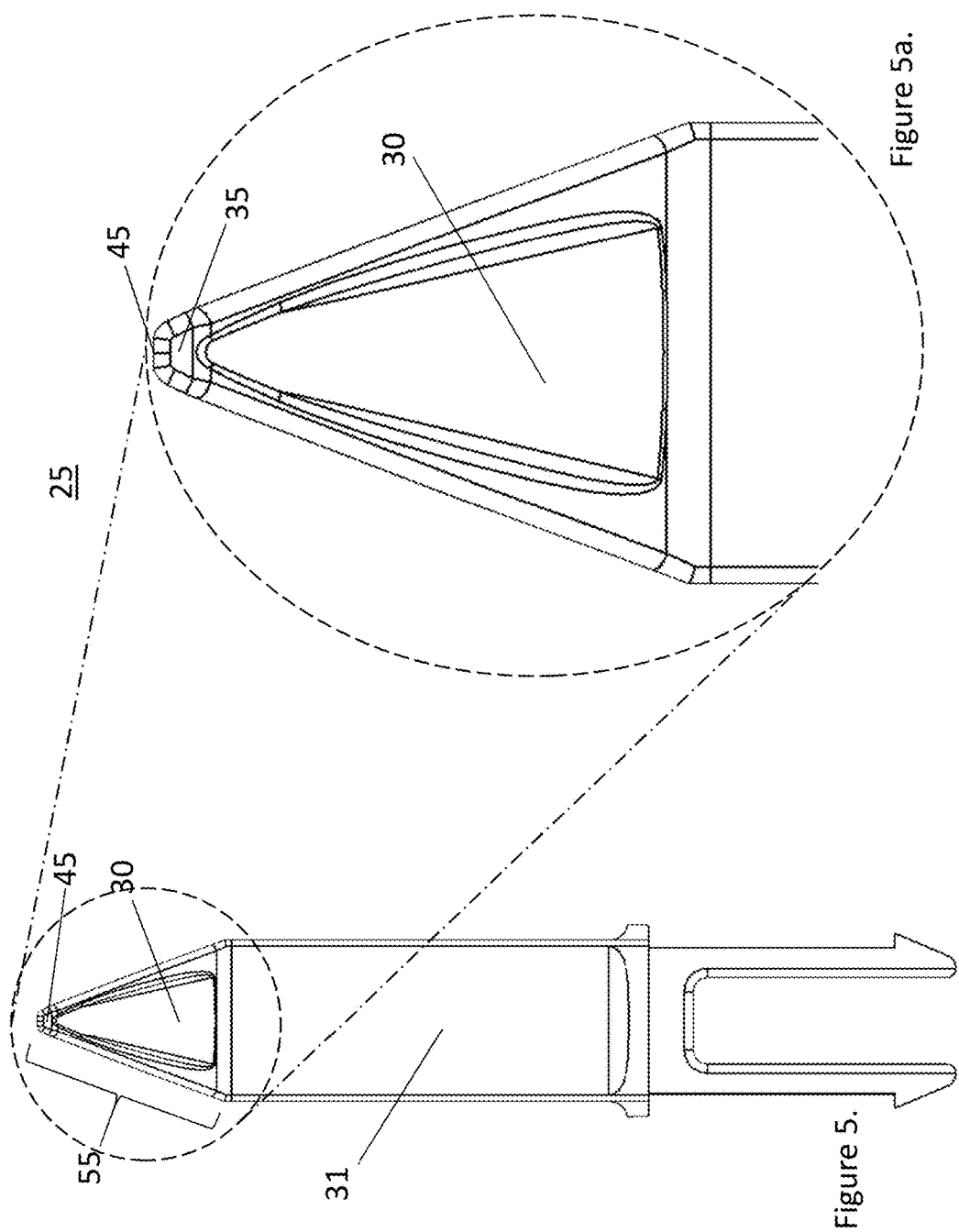
FIG. 5 is a frontal view of the digger, according to one embodiment of the present invention.

With reference to FIGS. 4 and 5 and according to one embodiment of the present invention the triangular zone 55 of the digger 25 is shown in greater detail. The triangular zone 55 contains a point that is rounded both in width and in length. The front facing point of the triangular zone 55 extends outwards, generating the protrusion 50. With specific reference to FIG. 4, the profile of the digger 25 is shown in greater detail. The protrusion 50 projects from the face 31 of the digger 25. As clearly shown in FIG. 4a, the first curved plane 40 contains a slight curve. The nub 35 connects the first curved plane 40 with the angle protrusion 50. With specific reference to FIG. 5, the face 31 of the digger 25 is shown in greater detail. The body of the digger 25 attenuates to a triangular zone 55. The triangular zone 55 contains a rounded edge 45 at the very point. As clearly shown in FIG. 5a, the triangular zone 55 is shown in greater detail. The tip of the triangular zone 55 contains rounded edges 45. The nub 35 connects the face of the triangular zone 55 with the rounded edge 45. The body of the triangular zone 55 contains a concave cavity. The cavity is present to lock the digger 25 with the nub 35. The close proximity of the digger 25 and nub 35 allows for a combination of these two elements which allows the cleaning of particles from under the fingernail region.

Figure 6:
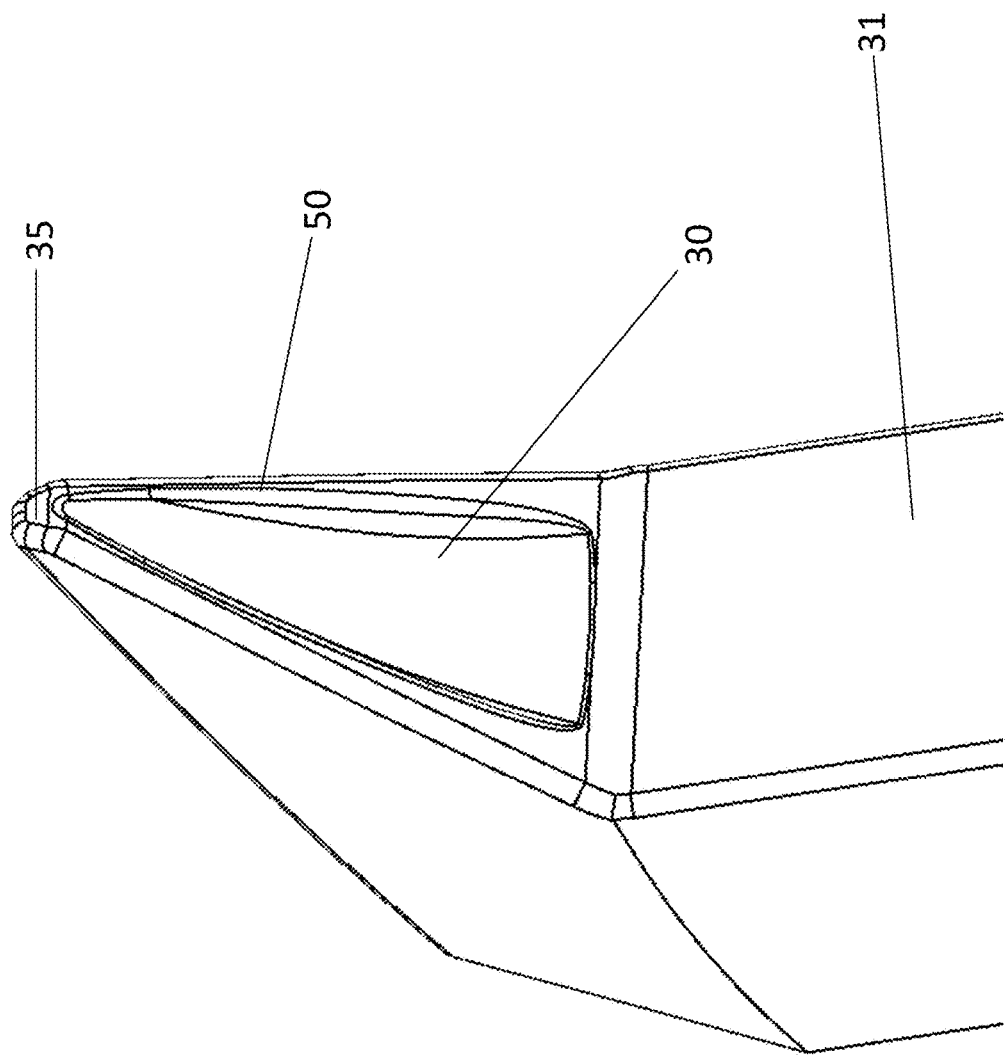
FIG. 6 is a perspective face view of the pointed tip of the digger, according to one embodiment of the present invention.

With reference to FIG. 6 and according to one embodiment of the present invention the protrusion 50 is shown in greater detail. The protrusion contains a concave cavity 30 within its face. The concave cavity 30 extends to the tip of the protrusion 50, and interacts with the nub 35. The tip of the concave cavity 30 penetrates the nub 35 and is flush with the external surface of the nub 35.

Figure 7:
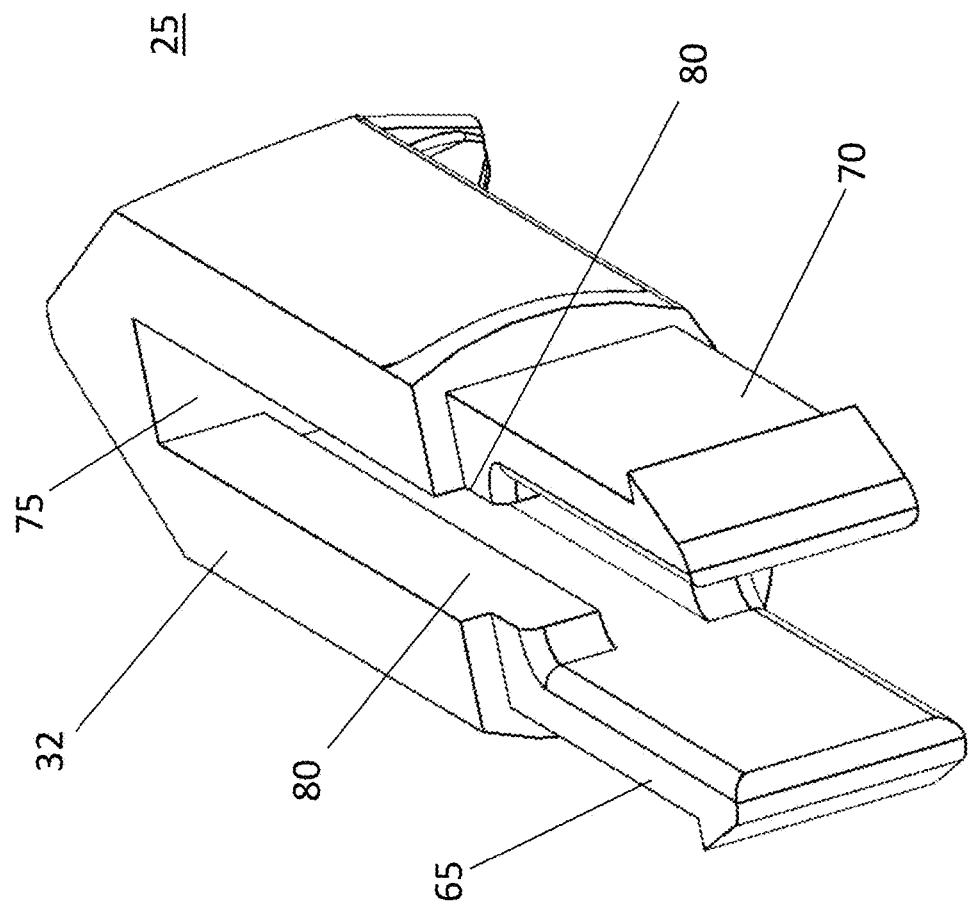
FIG. 7 is a perspective back view of the digger, according to one embodiment of the present invention.

With reference to FIG. 7 and according to one embodiment of the present invention the back 32 of the digger 25 is shown in greater detail. The back of the digger 25 contains a trough 75 framed by an open ended platform lip 80. The trough 75 extends out past the platform lip 80 to form the first and second arms, 65 and 70.

Figure 8A:
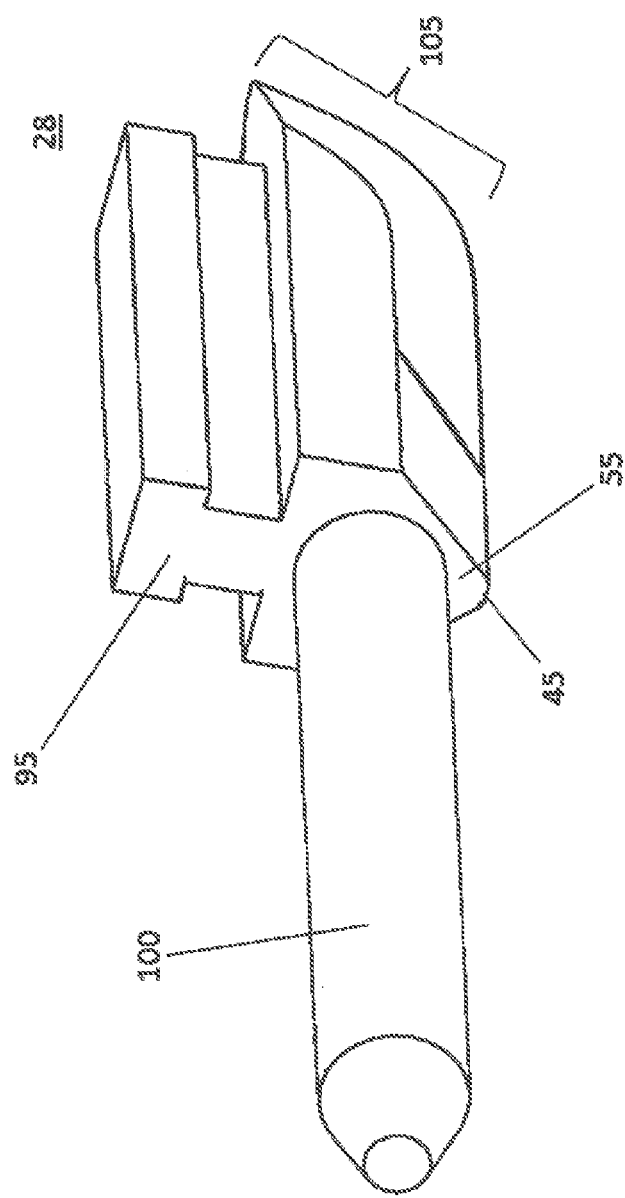
FIG. 8a is a perspective view of a nib as used in nail sanitizer tool, according to one embodiment of the present invention.
Figure 8B:
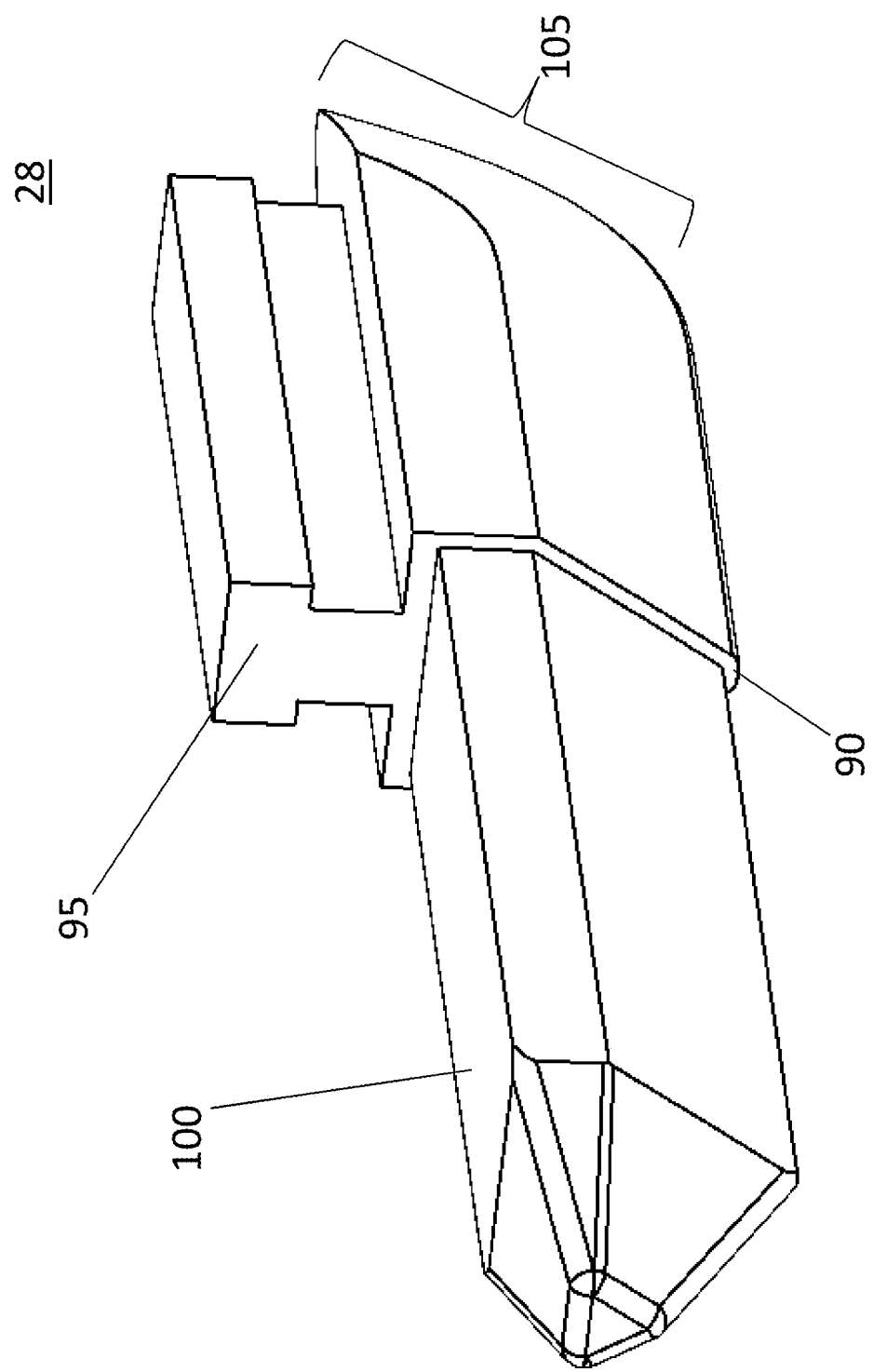
FIG. 8b is a perspective view of the nib, according to another embodiment of the present invention.
Figure 8C:
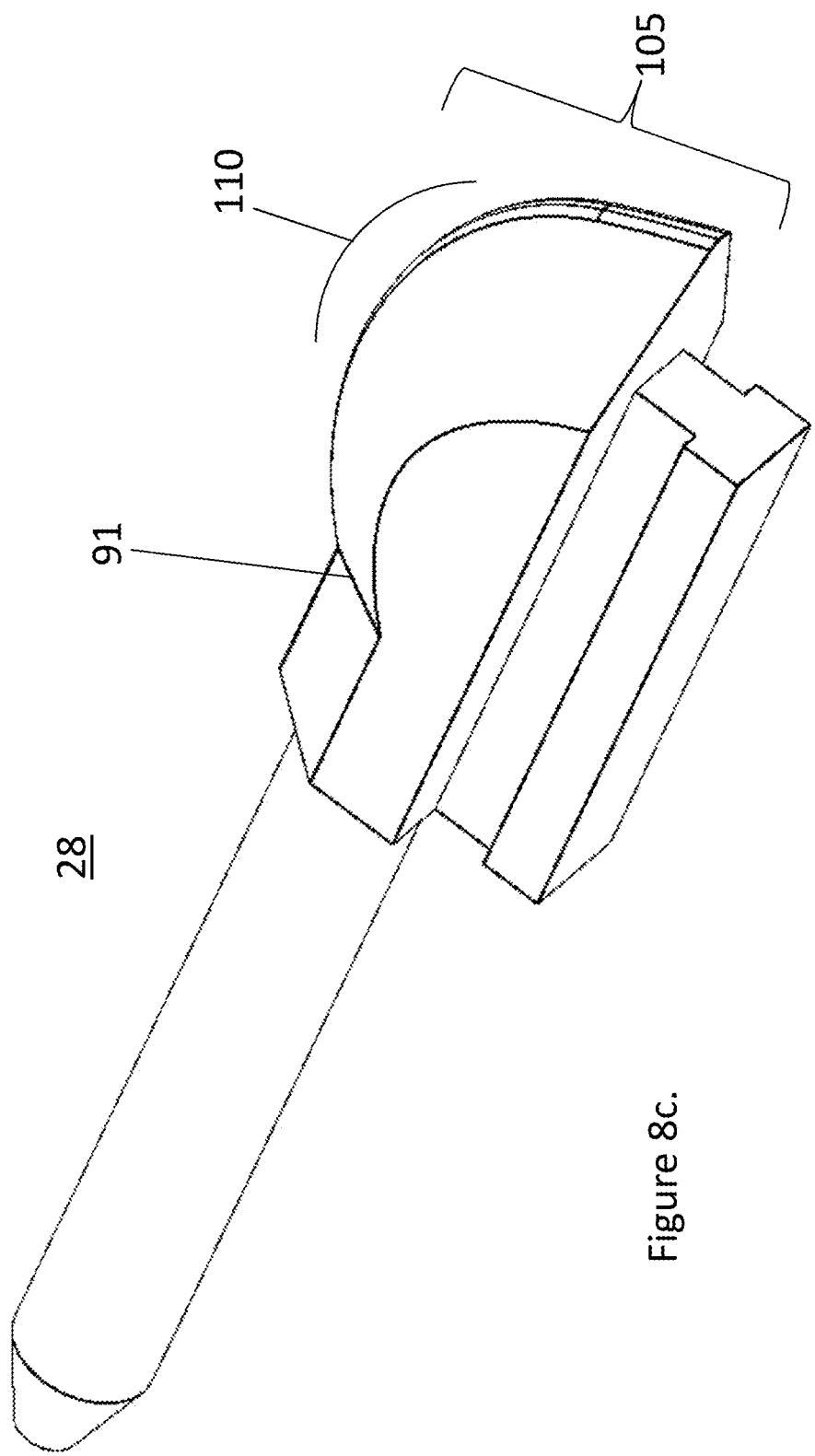
FIG. 8c is a perspective profile view of the nib, according to another embodiment of the present invention.

With reference to FIGS. 8a, 8b and 8c and according to an embodiment of the present invention the nib 28 is shown in greater detail. The nib 28 consists of: a T-shaped anchor 95; a connecting member extension 100; and an external member 105. The external member 105 contains a swooping curve. The triangular zone 55 is shown along the swooping curve of the nib 28. The triangular zone 55 tapers to a rounded edge 45 throughout the swooping curve. With specific reference to FIG. 8b, another embodiment of the nib 28 is shown. The connecting member extension 100 is triangularly shaped with a general width being slightly thinner than the external member 105. A worker skilled in the relevant art can appreciate the fact that the connecting member extension can be of any shape but must maintain a certain minimum length. The member extension must be of a minimum length in order to keep contact with other components of the nail sanitizer 5. With specific reference to FIG. 8c, another embodiment of the nib 28 is shown. The external member 105 contains a second circular plane 110 initiated at the curved slot 91. The nib 28 can be made of various materials as would be known by a worker skilled in the relevant art. In one embodiment, the nib is composed of a polypropylene which allows for passive saturation or capillary action as would be known to a worker skilled in the relevant art. The connecting member extension 100 through its contact with the wadding section (not shown) which wadding section (not shown) has alcohol, allows for the alcohol to travel from the wadding section (not shown) to the nib 28 through capillary action.

Figure 9:
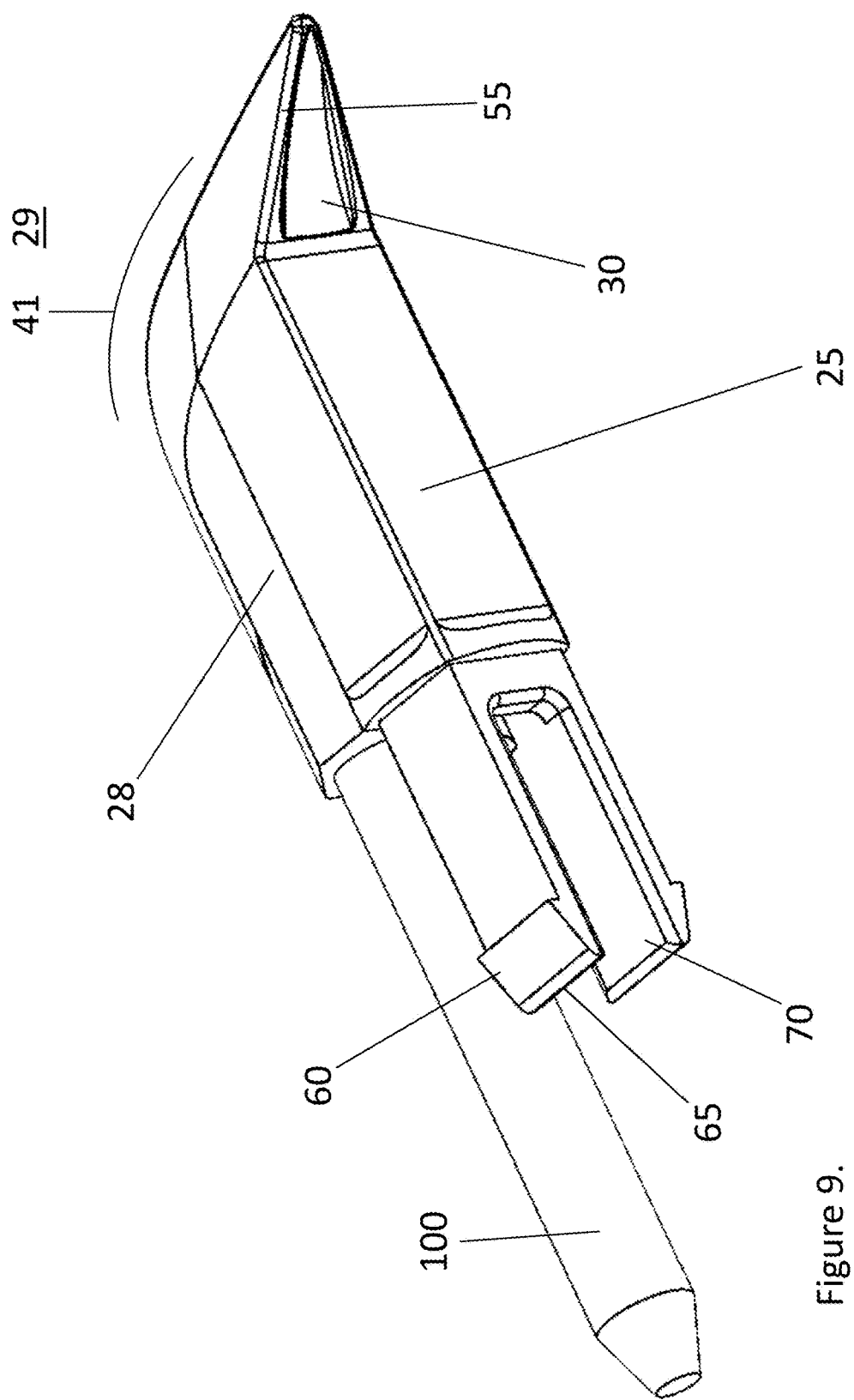
FIG. 9 is a perspective view of a nail penetrating device (digger coupled to the nib) as used in nail sanitizer tool, according to one embodiment of the present invention.
Figure 10:
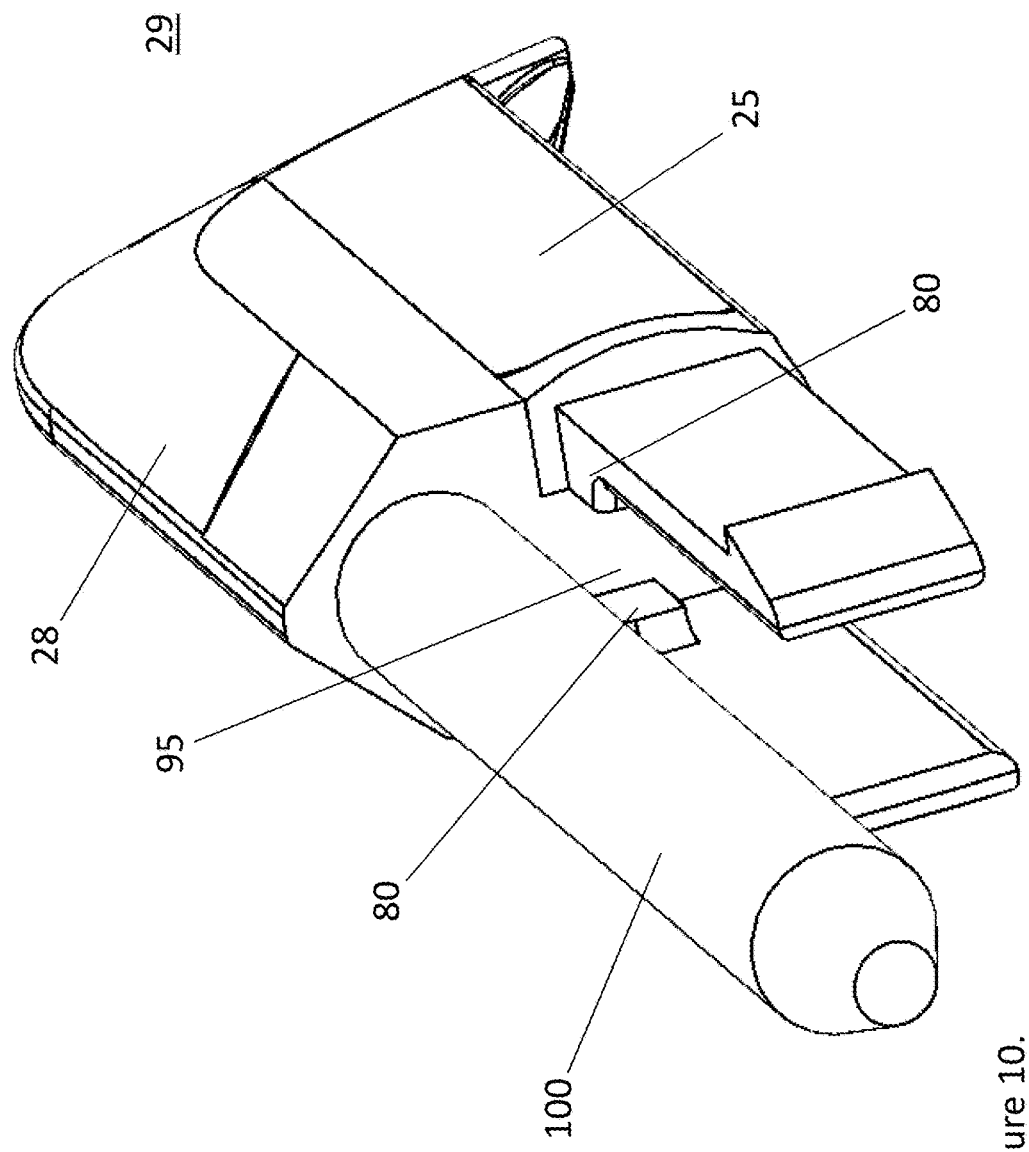
FIG. 10 is a perspective underside view of the nail penetrating device (digger coupled to the nib), according to one embodiment of the present invention.

With reference to FIGS. 9 and 10 and according to one embodiment of the present invention the nail penetrating device 29 is shown in greater detail. The nail penetrating device 29 is comprised of the digger 25 and a directly opposed nib 28. In another embodiment, the nail penetrating device 29 is composed on a single piece of material, having the digger 25 and the nib 28 directly opposed. When coupled together, the digger 25 and the nib 28 form a singular tool with a circular plane 41. The triangular zones 55 match to form a uniform continuous planar edge that is able to penetrate the UTF. In another embodiment, the circular plane 41 can also be a concave plane, or any other pattern which permits the user to insert the nail penetrating device 29 into the UTF and quickly and easily pass through the region. The connecting member extension 100 extends beyond the internal first and second arms 65 and 70. With specific reference to FIG. 10, the mating mechanism is shown in greater detail. The T-shaped anchor 95 is fastened within the hollow trough 75 (not shown) which is secured through the interaction with the open ended platform lip 80.

Figure 11A:
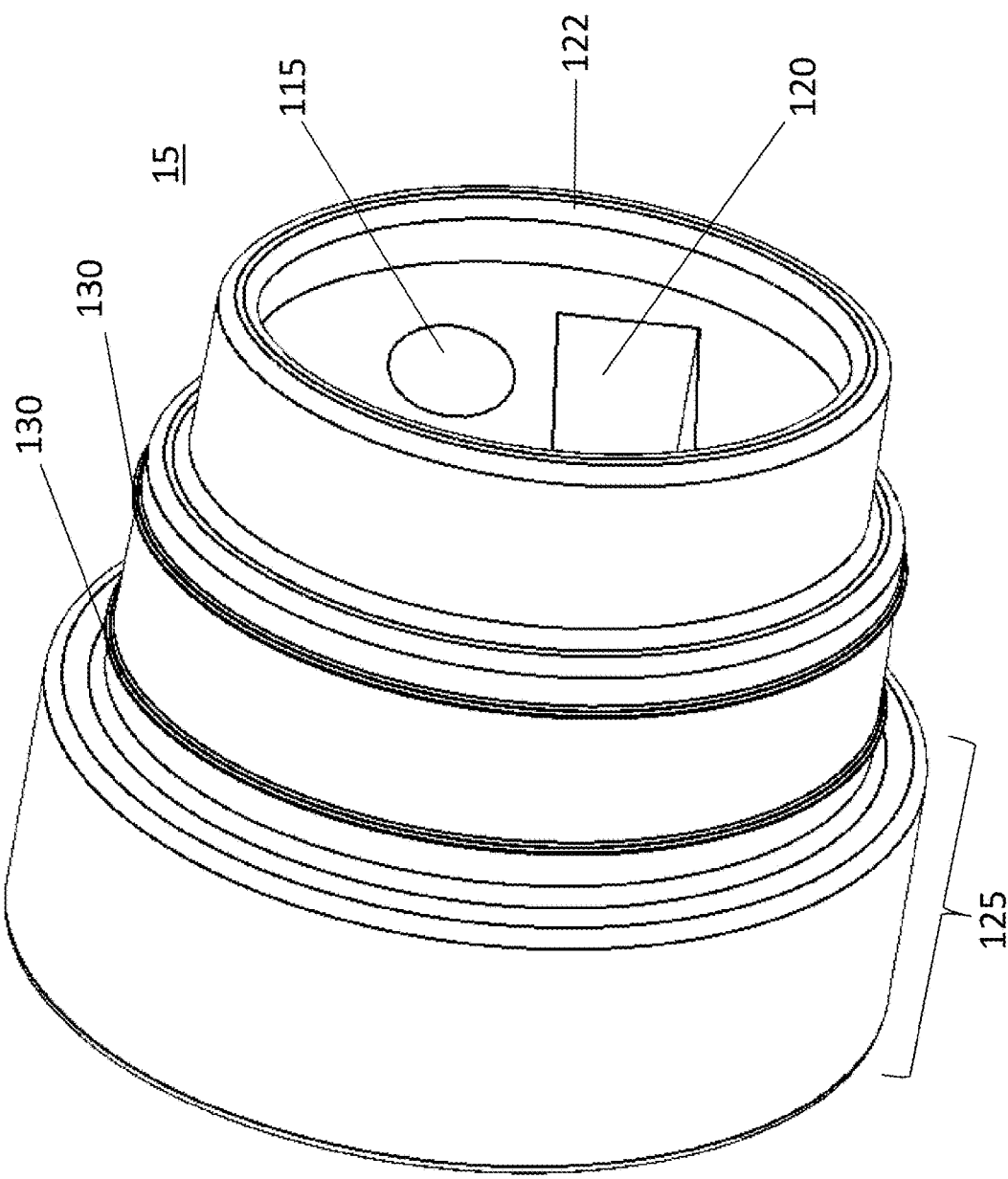
FIG. 11a is perspective view of a nib holder as used in nail sanitizer tool, according to one embodiment of the present invention.
Figure 11B:
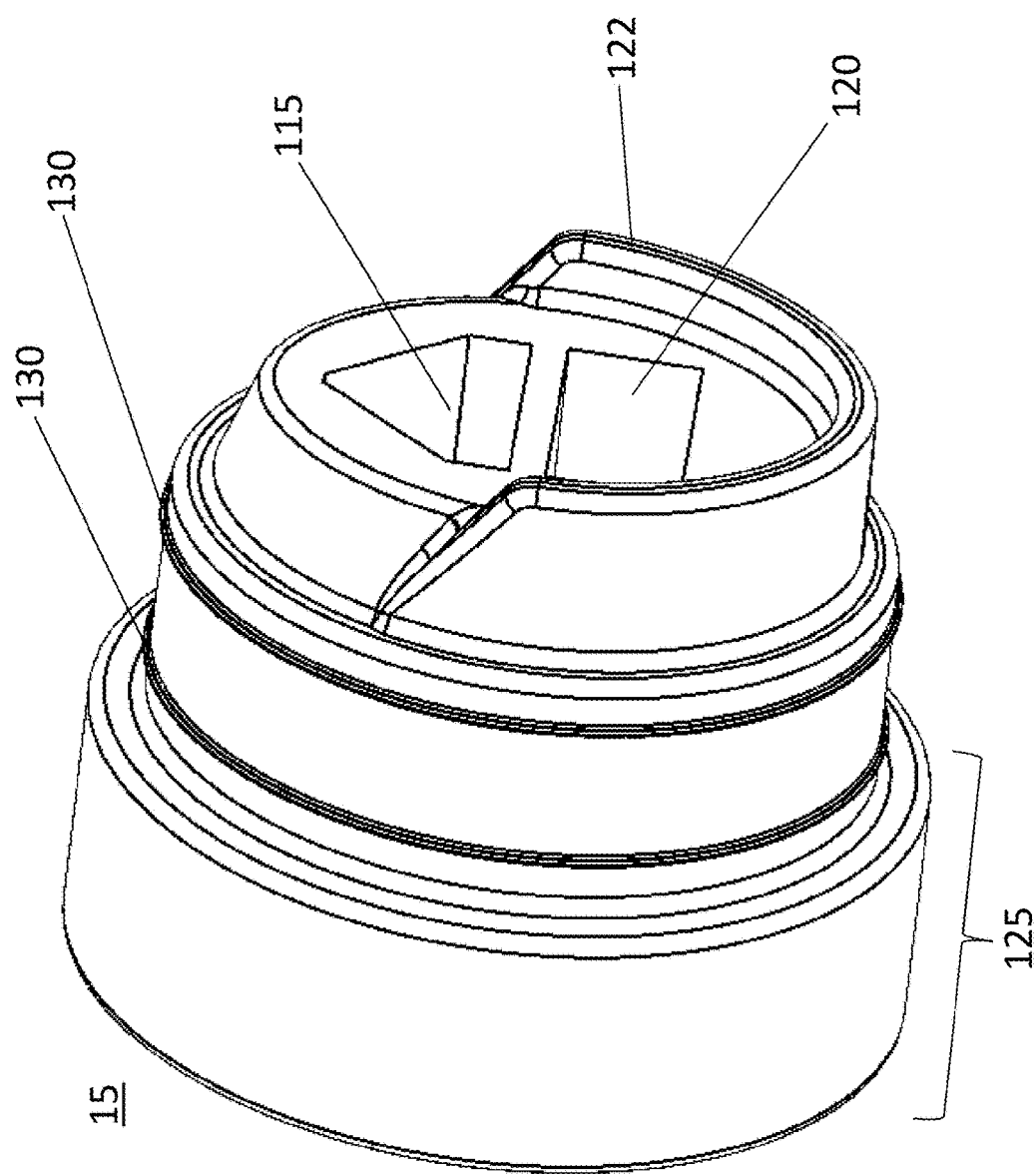
FIG. 11b is a perspective view of the nib holder, according to another embodiment of the present invention.

With reference to FIGS. 11a and 11b and according the present invention the nib holder 15 is shown in greater detail. First and second apertures 115 and 120 are positioned on an upper surface of the nib holder 15. The upper surface of the nib holder 15 is enclosed by the nib lip 122. The nib lip 122 functions to capture the falling debris the digger expels from the users UTF. First and second O-ring ribs 130 adorn the central region of nib holder 15. The lower region of the nib holder 15 extends out in a platform like manner forming the linking sleeve 125. With specific reference to FIG. 11b and according to another embodiment of the present invention the nib holder 15 is shown in greater detail. Only a portion of the upper surface of the nib holder 15 is enclosed by the nib lip 122. The nib lip 122 moulds into the body of the nib holder exposing the upper surface at the first aperture 115.

Figure 12:
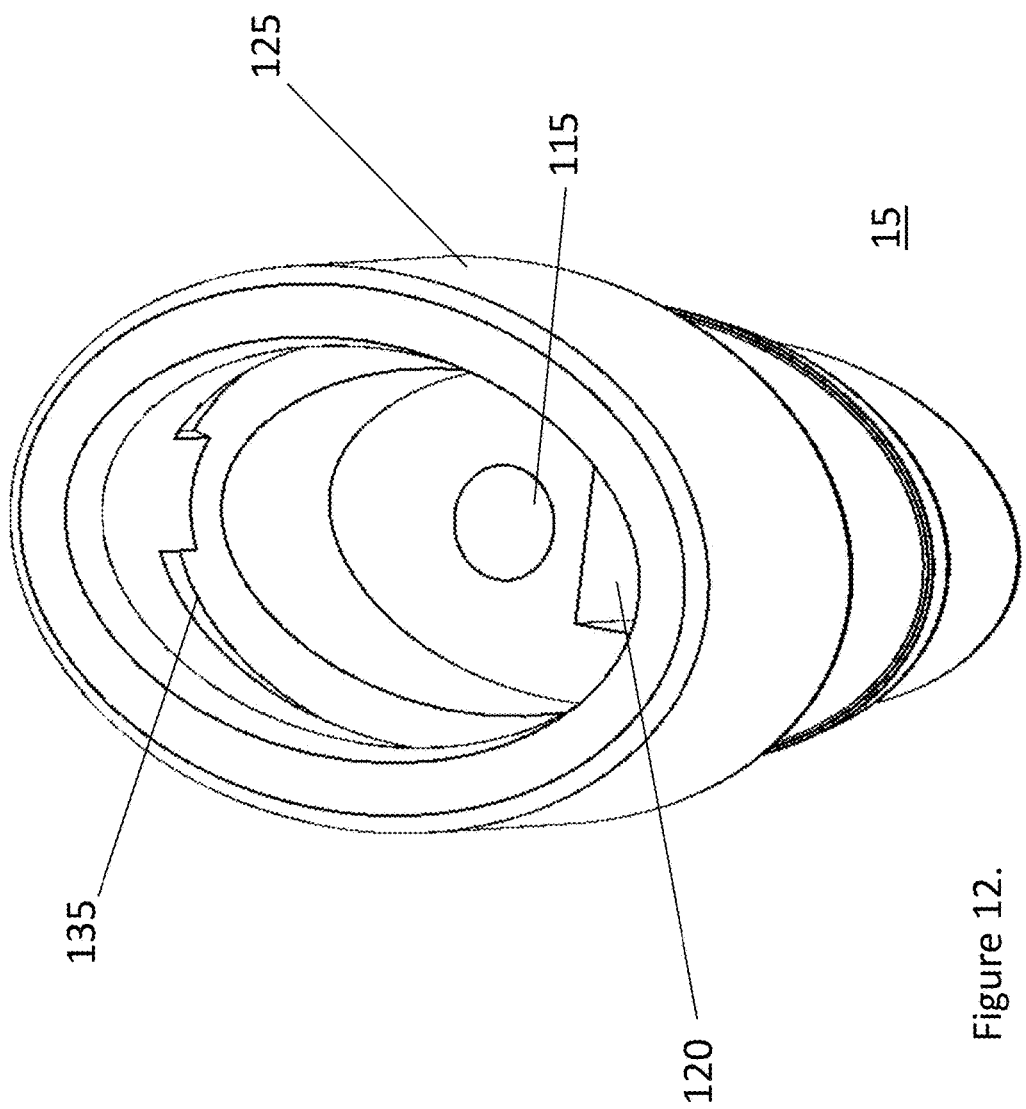
FIG. 12 is a perspective rear view of the nib holder shown in FIG. 11a, according to one embodiment of the present invention.

With reference to FIG. 12 and according to one embodiment of the present invention the inner region of the nib holder 15 is shown in greater detail. The first and second apertures 115 and 120 penetrate through the upper surface (not shown) and connect to the inner cavity of the nib holder 15. The inner region of the linking sleeve 125 contains a mounting bores 135.

Figure 13:
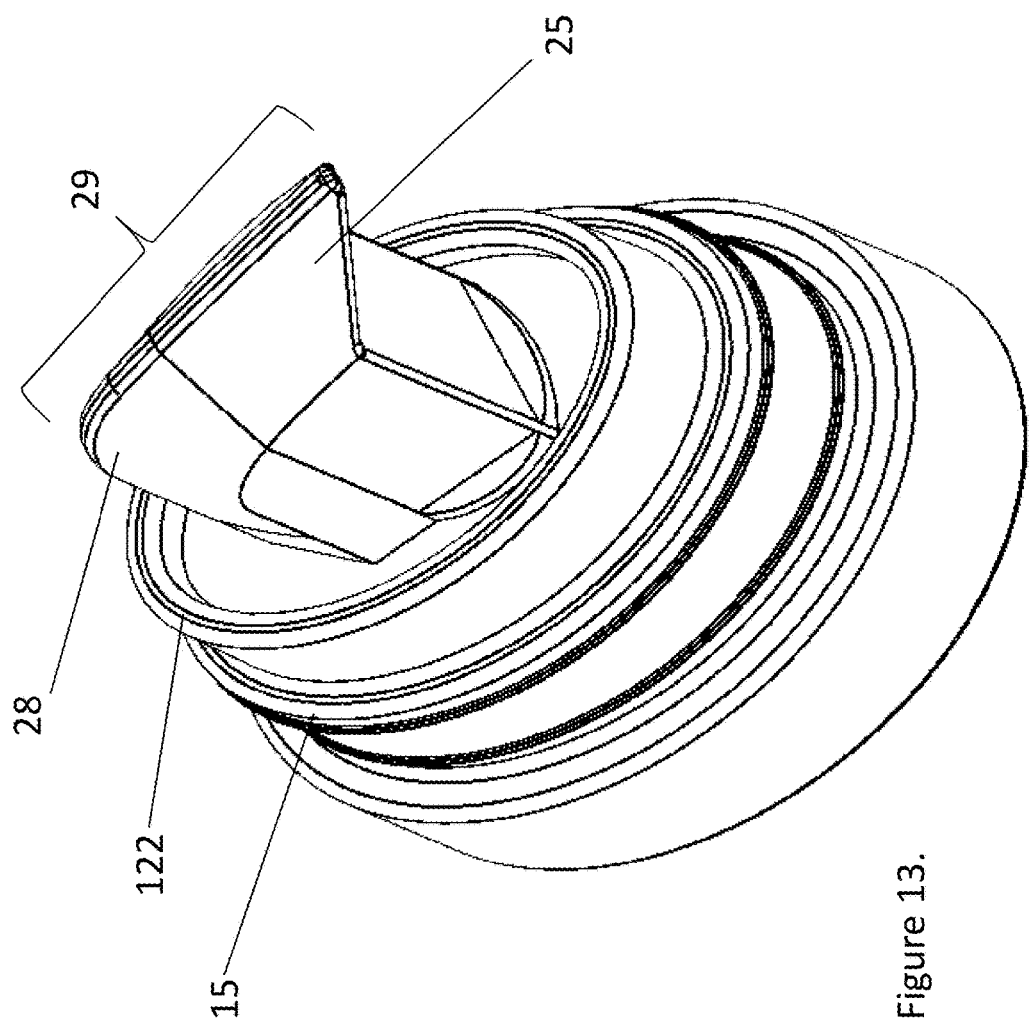
FIG. 13 is a perspective view of the nail penetrating device fastened to the nib holder, according to one embodiment of the present invention.
Figure 14:
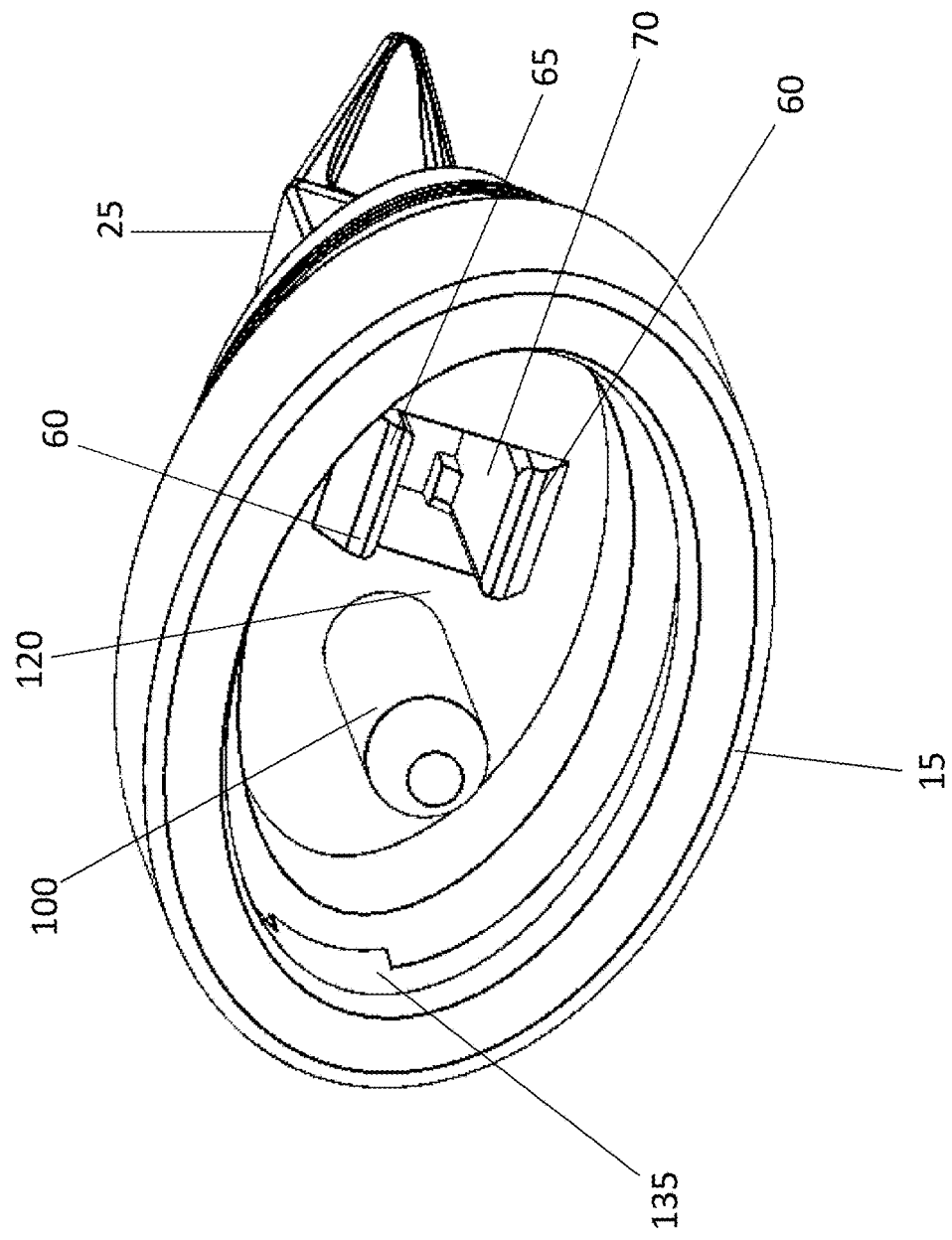
FIG. 14 is a perspective lower view of the nail penetrating device fastened to the nib holder, according to one embodiment of the present invention.

With reference to FIGS. 13 and 14 and according to one embodiment of the present invention the nail penetrating device 29 is shown attached to the nib holder 15. The nail penetrating device 29 is positioned on the upper surface of the nib holder 15. The upper surface of the nib holder is enclosed by the nib lip 122. With specific reference to FIG. 14 the interaction between the nail penetrating device 29 and the nib 28 is shown within the cavity of the nib holder 15. The connecting member extension 100 of the nib 28 and the first and second arms 65 and 70 of the digger pass through the first and second apertures 115, 120 of the nib holder 15, respectively. The nail penetrating device 29 is fastened to the nib holder 15 through the interaction of the first and second arms 65 and 70 of the digger 25 with aperture 120. The extruding latches 60 of the first and second arms 65 and 70 mount onto the inner cavity edge of the aperture 120. A worker skilled in the relevant art would appreciate the various mounting methods that can be used to fasten the nail penetrating device 29 to the nib holder. In another embodiment of the present invention, the nail penetrating device 29 and the nib 28 is constructed from a single piece of material.

Figure 15:
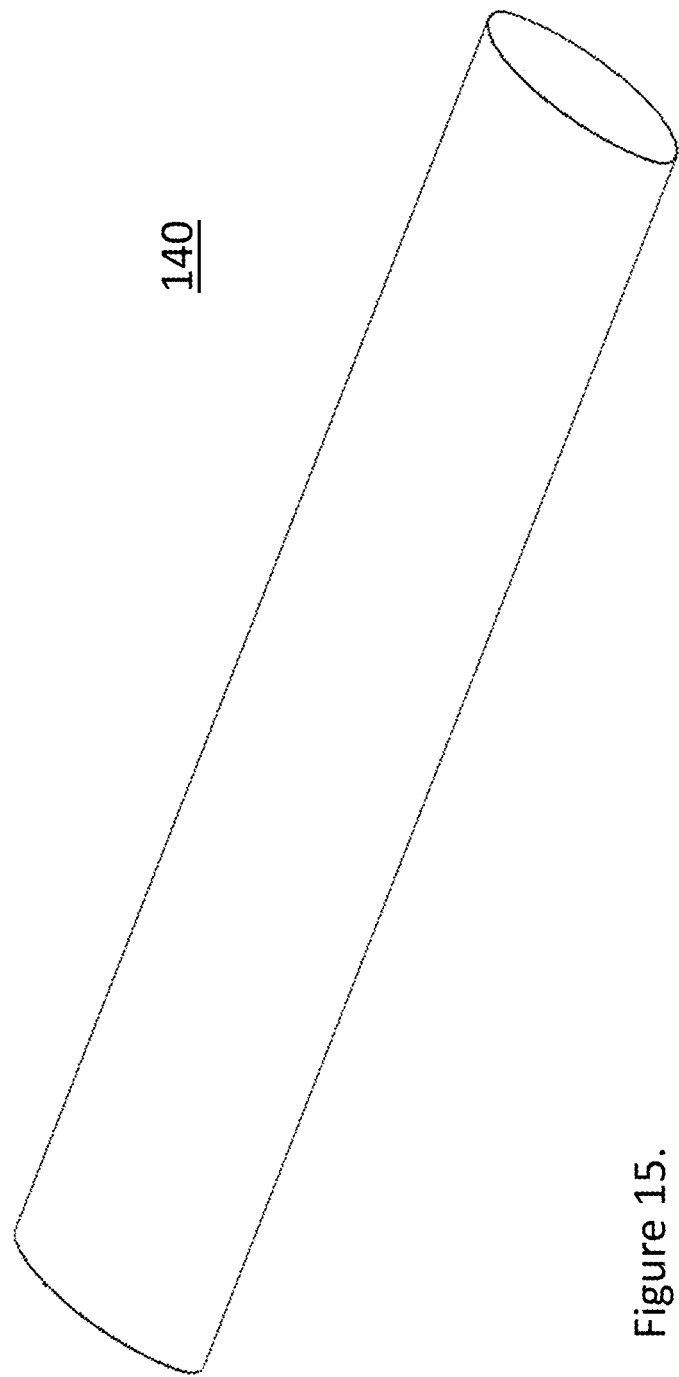
FIG. 15 is a perspective view of a wadding section as used in nail sanitizer tool, according to one embodiment of the present invention.

With reference to FIG. 15 and according to one embodiment of the present invention the wadding section 140 is shown in greater detail. The wadding section 140 shape is dependent on the shape and size of the nail sanitizer main body 20 (not shown). The wadding section 140 can be composed of various materials such as sponge material, cotton or any alcohol conducive material as would be known by a worker skilled in the relevant art. The wadding section can also be comprised on the sanitizing solution only, wherein the operation of the nail sanitizer tool 5, requires inversion.

Figure 16:
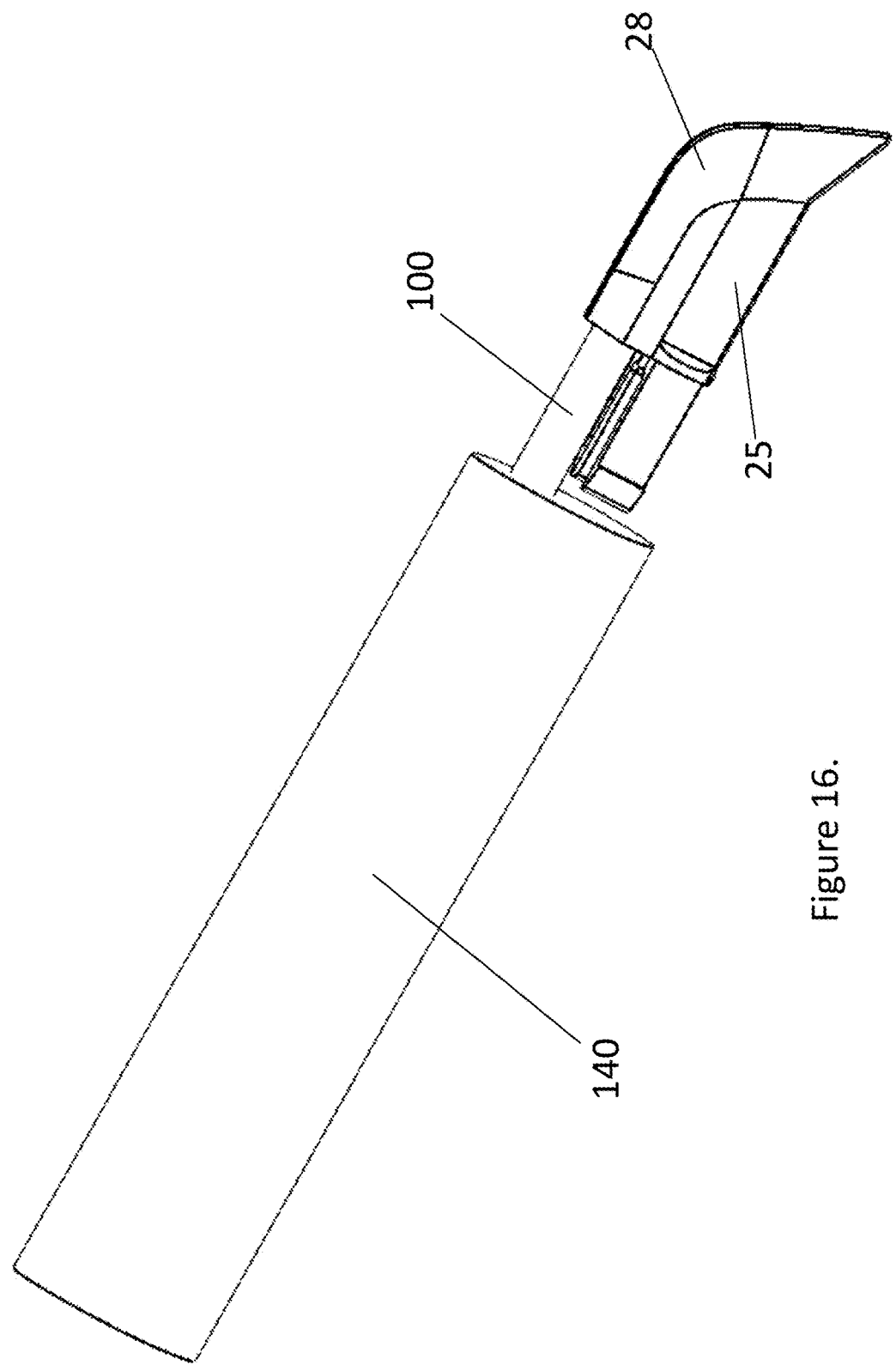
FIG. 16 is a perspective view of the nail penetrating device mounted to the wadding section, according to one embodiment of the present invention.

With reference to FIG. 16 and according to one embodiment of the present invention the nail penetrating device 29 is shown in fluid communication with the wadding section 140. The connecting member extension 100 of nib 28 penetrates the top surface of the wadding section 140. The minimal length ensures the required interaction between the nib 28 and the wadding section 140.

Figure 17:
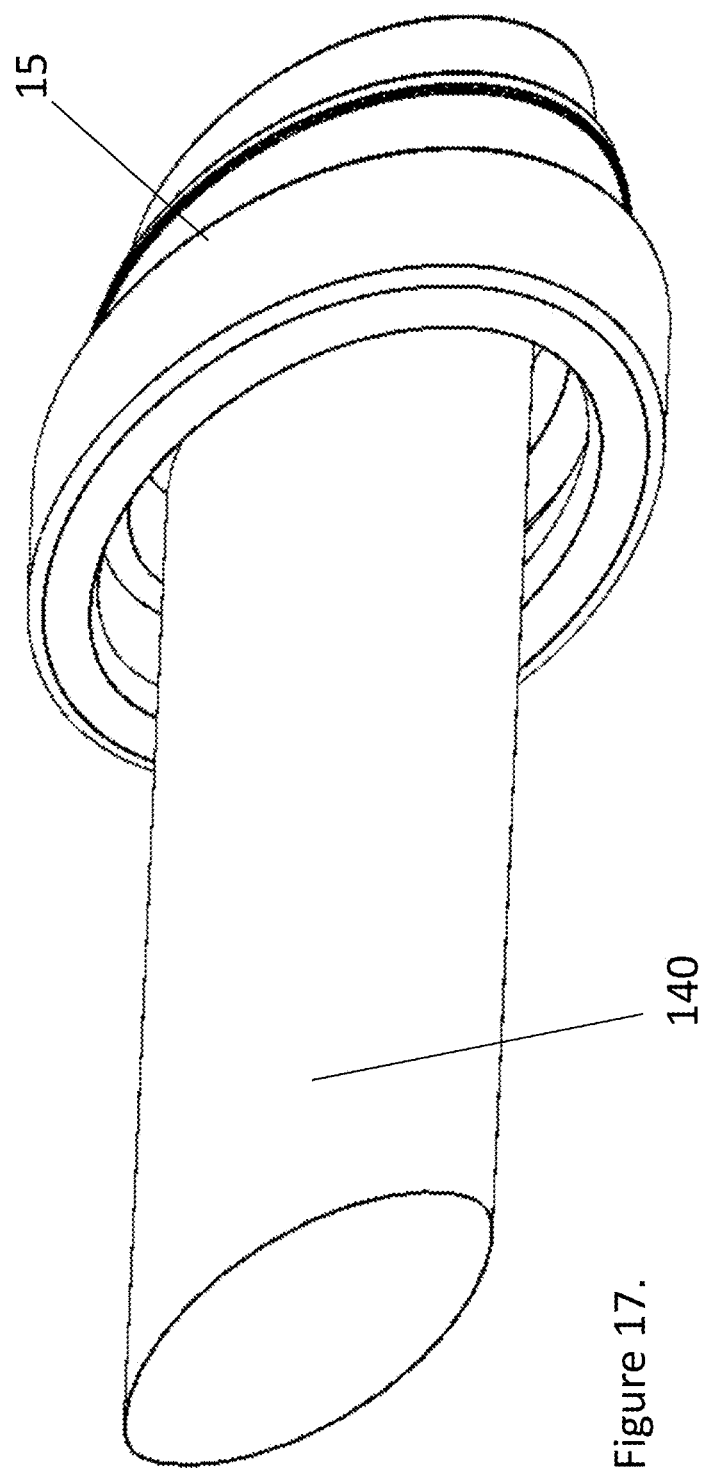
FIG. 17 is a perspective view of the wadding section set within the nib holder, according to one embodiment of the present invention.

With reference to FIG. 17 and according to one embodiment of the present invention the wadding section 140 is shown fitted within the nib holder 15. The wadding section 140 rests within the cavity of the nib holder 15.

Figure 18:
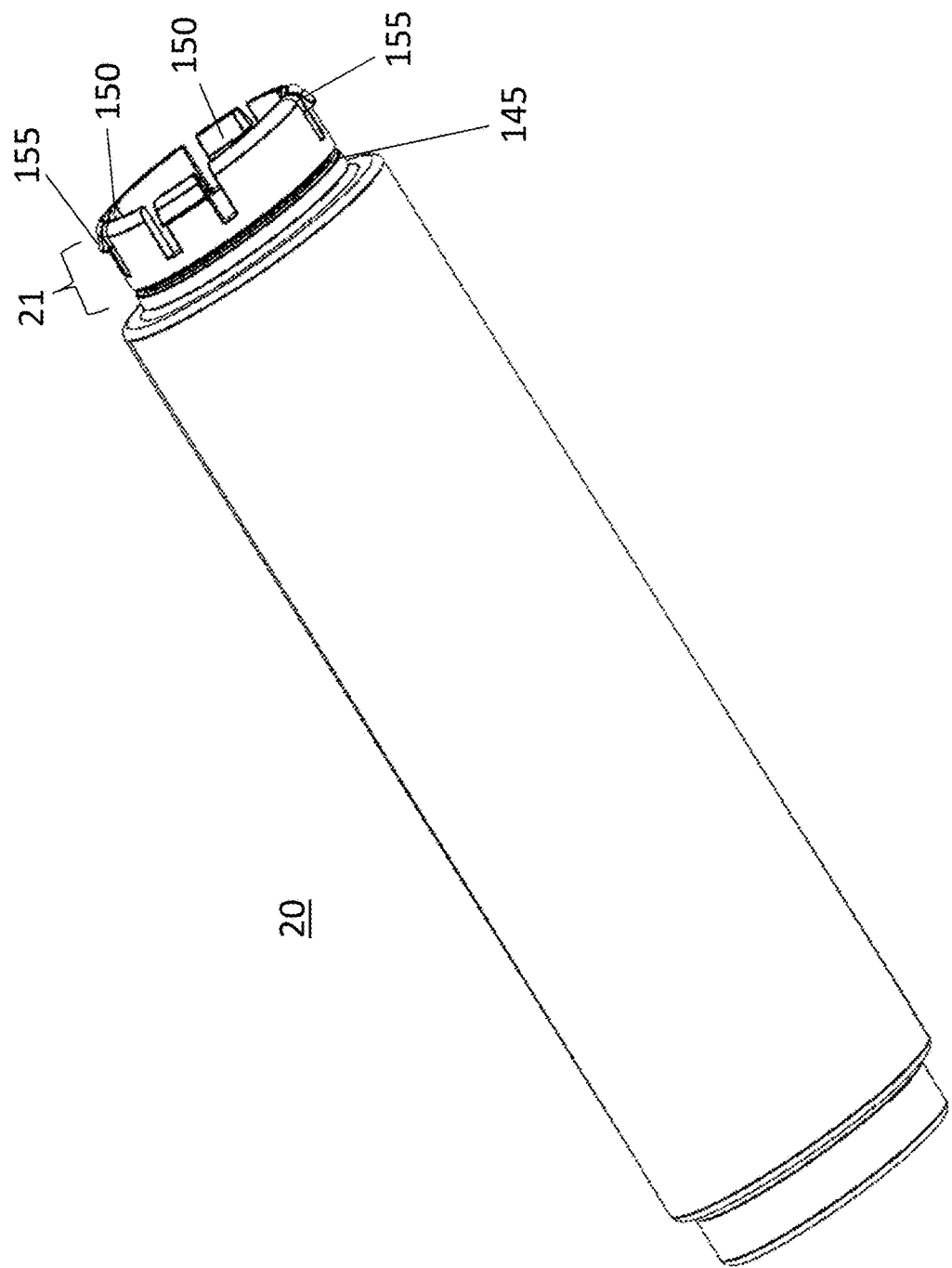
FIG. 18 is a perspective view of a main body as used in nail sanitizer tool, according to one embodiment of the present invention.

With reference to FIG. 18 and according to one embodiment of the present invention the main body 20 is shown in greater detail. A plurality of latches 150 adorns the upper neck 21 of the main body 20. A number of the latches 150 contain clip protrusions 155 extending out from the surface of the main body 20. An O-ring seal 145 wraps around the lower portion of main body neck 21.

Figure 19:
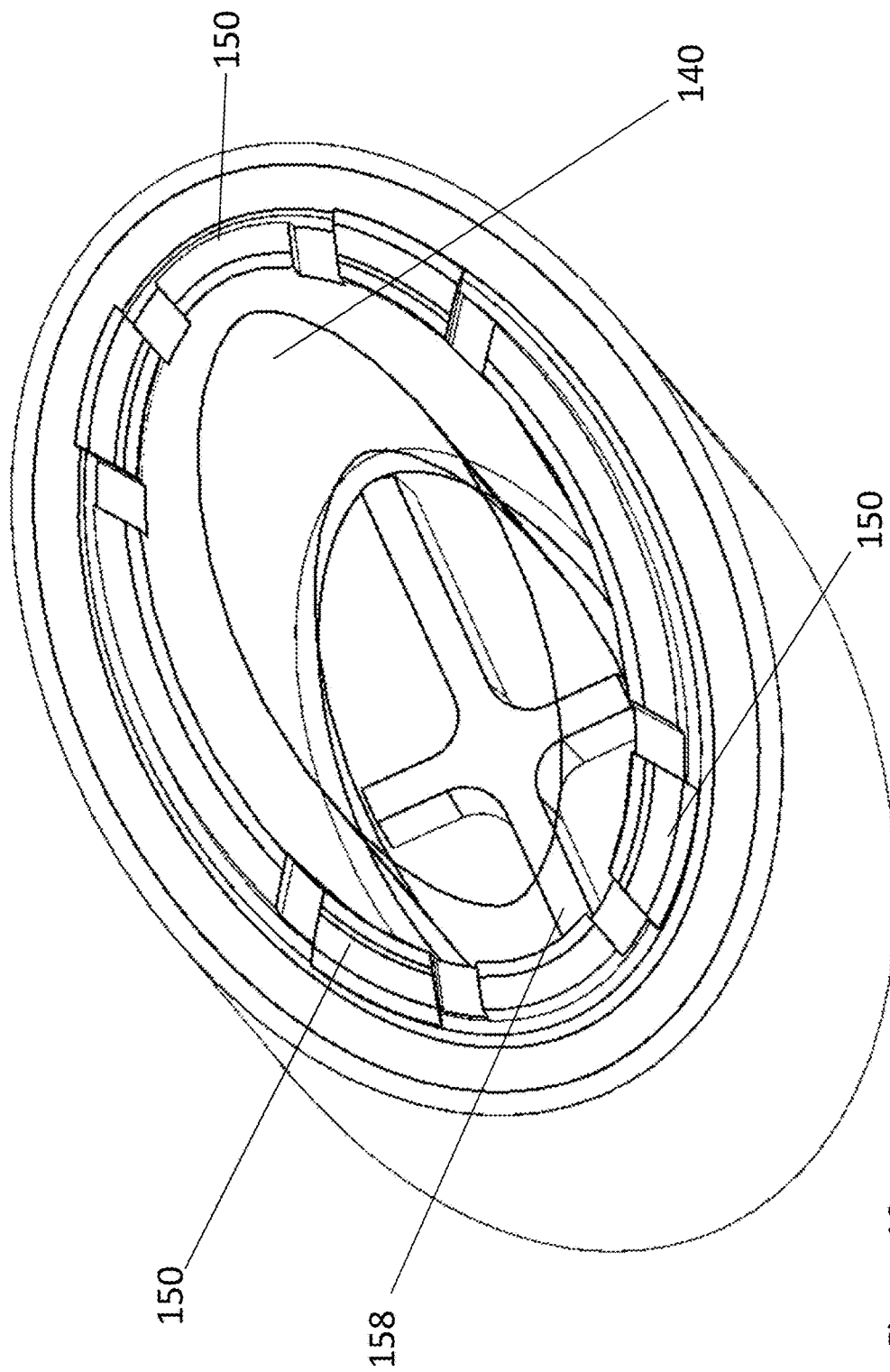
FIG. 19 is a perspective aerial view of the main body housing the wadding section, according to one embodiment of the present invention.

With reference to FIG. 19 and according to one embodiment of the present invention the wadding section 140 is shown fitted within main body 20. The wadding section 140 shape and size is dependent upon fitting within the main body 20. The wadding section 140 is shown as transparent for illustrative purposes. The ribs 158 on the interior floor of the main body 20 accurately position the wadding section 140.

Figures 20, 20A:
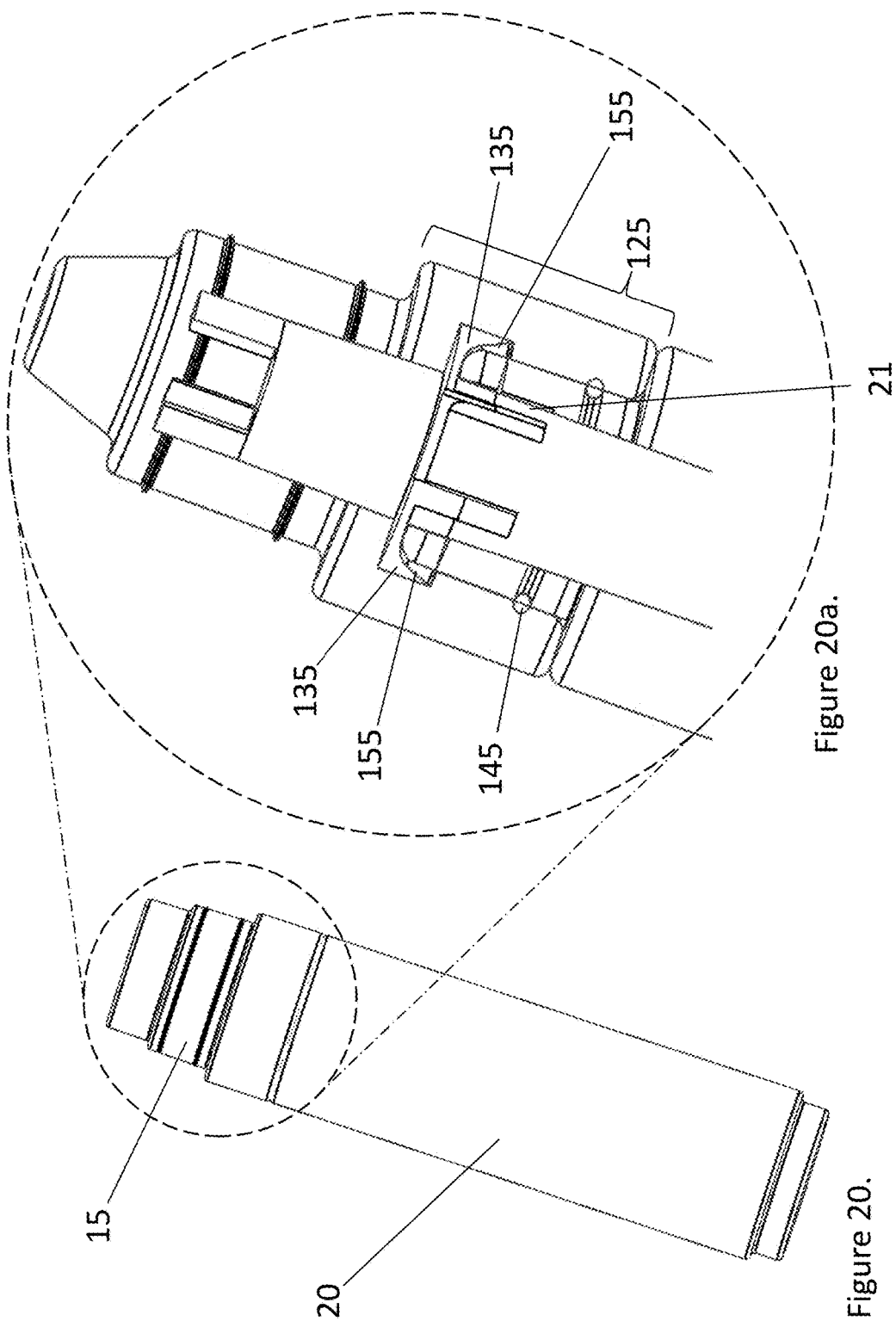
FIG. 20 is a perspective view of the main body latched to the nib holder, according to one embodiment of the present invention.
FIG. 20a is a perspective cross-sectional view of a nib holder latching onto the main body, according to one embodiment of the present invention.

With reference to FIGS. 20 and 20a and according to one embodiment of the present invention the nib holder 15 is shown connected to the main body 20. The nib holder 15 fits over the neck 21 region of the main body 20. With specific reference to FIG. 20a the connection mechanism is shown in greater detail. A cross-sectional view of the nib holder connected to the body is shown in order to illustrate the connecting mechanism. The O-ring seal 145 fastens the nib holder 15 to the main body 20. The clip protrusions 155 hook into the mounting bore 135 within the inner surface of the linking sleeve 125. A worker skilled in the relevant art would appreciate the various mounting mechanisms that can be employed to connect the nib holder 15 to the main body 20.

Figure 21:
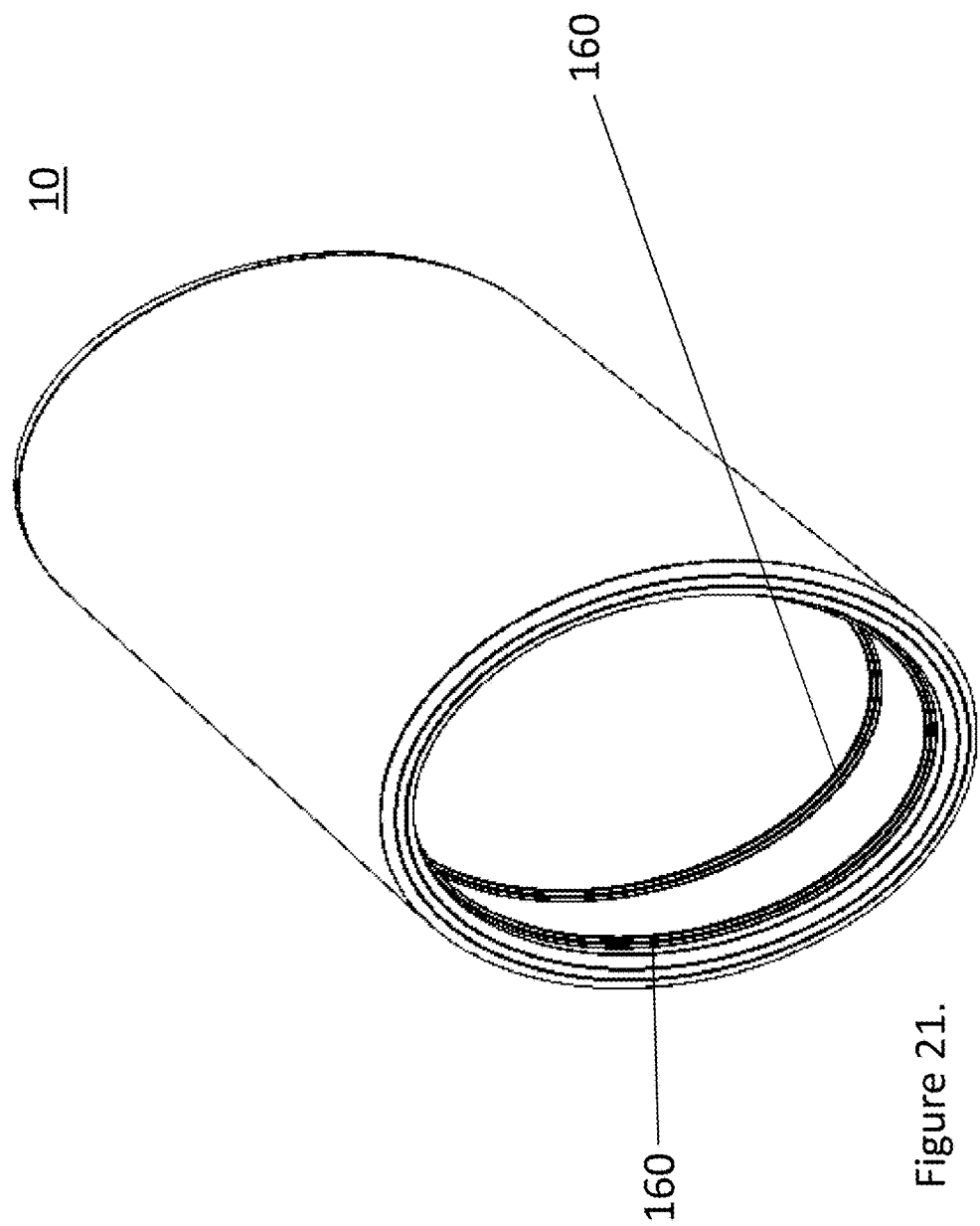
FIG. 21 is a perspective view of a cup as used in nail sanitizer tool, according to one embodiment of the present invention.

With respect to FIG. 21 and according to one embodiment of the present invention the cap 10 is shown in greater detail. The cap 10 contains two inner surface O-ring grooves 160 positioned near the cap opening.

Figure 22:
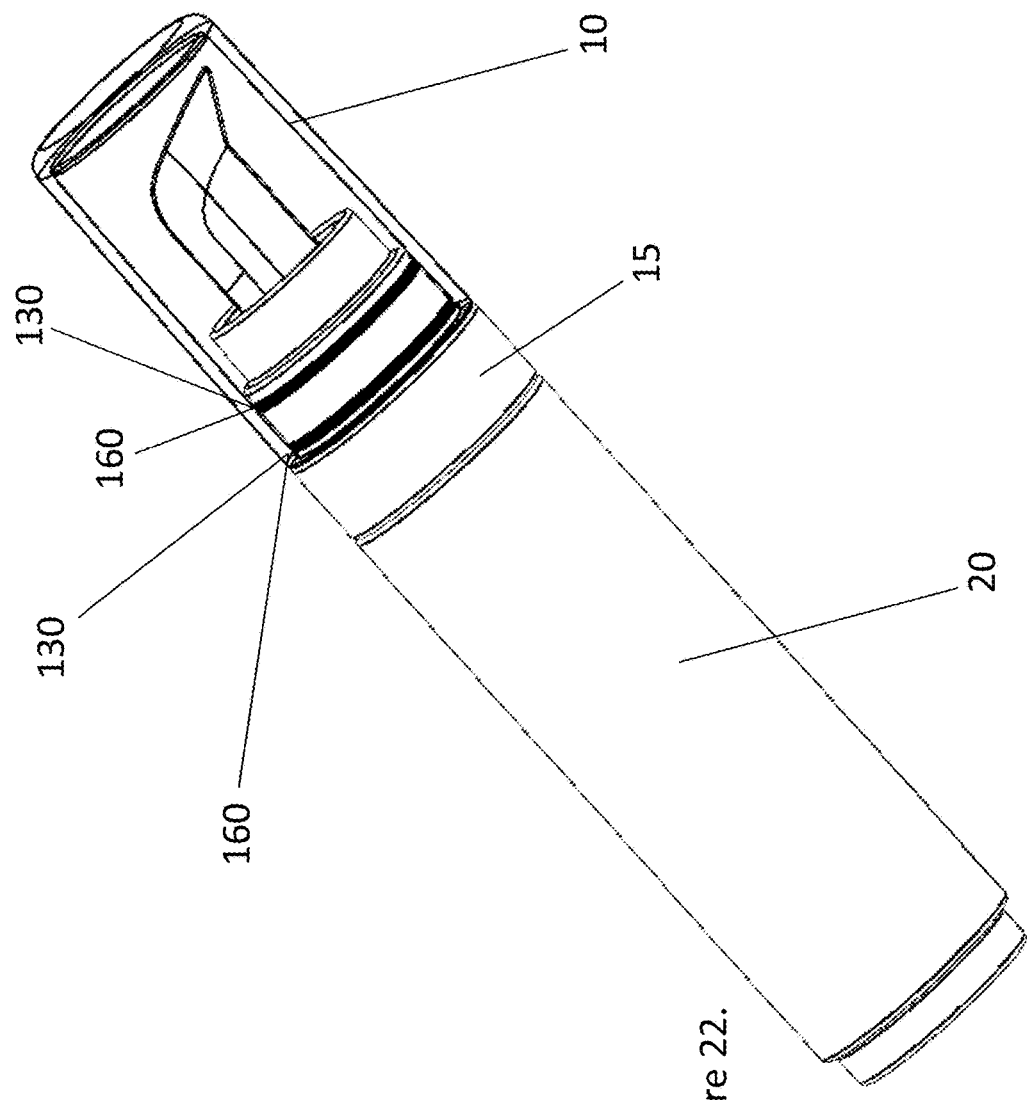
FIG. 22 is a perspective view of the body, nib holder, and the cup, according to one embodiment of the present invention.

With respect to FIG. 22 and according to one embodiment of the present invention the nail sanitizer tool 5 is shown in greater detail. The nail sanitizer tool 5 is primarily comprised of: the main body 20; cap 10; nib holder 15; digger 25; nib 28; and wadding section (not shown). The cap is secured onto the nib holder 15 through the interaction of its O-ring grooves 160 with the O-ring ribs 130 of the nib holder 15. The nib holder 15 connects the main body 20 with the nail penetrating device 29, consisting of the digger 25 and the nib 28.

Although the invention has been described above by reference to certain embodiments of the invention, the invention is not limited to the embodiments described above. Modifications and variations of the embodiments described above will occur to those skilled in the art in light of the above teachings. Moreover, with respect to the above description, it is to be repulsed that the optimum dimensional relationships for the component members of the present invention may include variations in size, material, shape, form, funding and manner of operation.

Having thus described the invention, it is now claimed.

We claim:

1. A nail cleaning and sanitizing tool comprising:
a) a main body housing a wadding section to store alcohol;
b) a nail penetrating device connected to and in fluid communication with the main body, the nail penetrating device further comprising:
   i. a digger comprised of a body having a proximal portion, a tapered distal portion and a protrusion extending from a first side of the body adjacent the tapered distal portion, the protrusion forming a triangle pyramid shape having one face thereof a concave cavity bound along a periphery by first and second retaining walls, where the first and second retaining walls form edges between the one face and another two faces of the triangular pyramid shape and converge at an apex of the triangular pyramid to form a nub, wherein a continuous distal edge of the digger is formed by a distal-most edge of the tapered portion, a distal-most edge of the protrusion and the nub, where the nub is adjacent and continuous with the distal-most edge of the protrusion and disposed opposite the tapered portion, and,
   ii a nib, the nib having a first side and a second side joined at one end by a wall, where the first and second sides converge and terminate at a curved peripheral edge opposite the wall, and wherein the nib is in fluid communication with the wadding section and the wall of the nib is directly coupled to a second side of the body of the digger opposite the first side,
c) wherein the curved peripheral edge provides optimal contact to sanitize an under the nail region, and,
d) wherein the concave cavity and the first and second retaining walls terminating in the nub remove and collect debris from the under the nail region.

2. The nail sanitizing tool according to claim 1 further comprising a nib holder interconnecting the nib and the main body.

3. The nail sanitizing tool according to claim 1 wherein the nib further comprises:
a) an anchor that connects the nib with the digger to form the nail penetrating device; and
b) a connecting member extension, completing the fluid communication with the wadding section and the nib.

4. The nail sanitizing tool according to claim 1, wherein the nib further comprises a porous material that allows for passive saturation or capillary action of the sanitizing solution from the wadding section thereby allowing the nib to deposit the sanitizing solution in the under the nail region as it passes through the under the region.

5. The nail sanitizing tool according to claim 1, wherein the wadding section further comprises an absorbent material housing a sanitizing solution.

6. The nail sanitizing tool according to claim 1, wherein the wadding section farther comprises a bladder housing a sanitizing solution.

* * * * *